United States Patent [19]

Hara et al.

[11] Patent Number: 5,162,318

[45] Date of Patent: Nov. 10, 1992

[54] BENZIMIDAZOLINONE DERIVATIVES

[75] Inventors: Hiromu Hara, Chiba; Tatsuya Maruyama, Ibaraki; Munetoshi Saito, Ibaraki; Makoto Takeuchi, Ibaraki; Toshiyasu Mase, Chiba, all of Japan

[73] Assignee: Yamanouchi Pharmaceutical Co., Ltd., Tokyo, Japan

[21] Appl. No.: 684,866

[22] Filed: Apr. 15, 1991

[30] Foreign Application Priority Data

Apr. 13, 1990 [JP] Japan .................. 2-98455
Oct. 23, 1990 [JP] Japan .................. 2-285493

[51] Int. Cl.$^5$ ............... A61K 31/535; A61K 31/445; A61K 31/415
[52] U.S. Cl. .................. 514/234.5; 514/322; 514/387
[58] Field of Search ............... 548/305; 514/387, 322, 514/234.5

[56] References Cited

U.S. PATENT DOCUMENTS

| | | | |
|---|---|---|---|
| 4,154,829 | 5/1979 | Mentrup et al. | 548/305 |
| 4,200,641 | 4/1980 | Vandenberk et al. | 514/318 |
| 4,256,756 | 3/1981 | Koppe et al. | 548/305 |
| 4,492,708 | 1/1985 | Spitzer | 548/305 |

FOREIGN PATENT DOCUMENTS 0058975 9/1982 European Pat. Off.
62-252721 4/1987 Japan.

OTHER PUBLICATIONS

Davall et al., "Some N-substituted 2-oxobenzimidazolines" J. Chem. Soc., 1960, pp. 314–318.

*Primary Examiner*—Mary C. Lee
*Assistant Examiner*—Mary Susan H. Gabilan
*Attorney, Agent, or Firm*—Burgess, Ryan and Wayne

[57] ABSTRACT

Benzimidazolinone derivatives of the general formula (I):

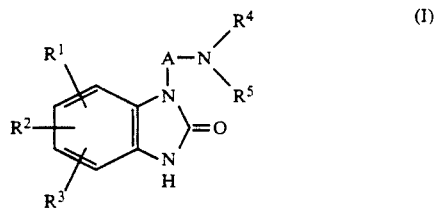

wherein $R^1$, $R^2$ and $R^3$, which may be the same or different, each is a hydrogen or halogen atom or a lower alkyl, halo-lower alkyl, hydroxy-lower alkyl, hydroxyl, lower alkoxy, aryloxy, acyl, cyano, carboxyl, a lower alkoxycarbonyl, carbamoyl, nitro or nitrogen-containing 5- or 6-membered heterocyclic group; A is an ethylene group which may optionally have at least one branch; $R^4$ and $R^5$, which may be the same or different, each is a lower alkyl group or $R^4$ and $R^5$, together with the adjacent nitrogen atom, represent a pyrrolidinyl, piperidino or a morpholino group provided that when

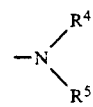

is a piperidino or diethylamino group, at least one of $R^1$, $R^2$ and $R^3$ is other than a hydrogen atom, or pharmaceutically acceptable salts thereof, methods of producing the same and pharmaceutical compositions containing the same are disclosed. Pharmacologically, the above compounds (I) have pulmonary surfactant secretion promoting activity.

8 Claims, No Drawings

BENZIMIDAZOLINONE DERIVATIVES

FIELD OF THE INVENTION

The present invention relates to novel substituted benzimidazolinone derivatives and salts thereof, which are of value as drugs, particularly as pulmonary surfactant secretion stimulants.

BACKGROUND OF THE INVENTION

A physiologically active substance, called "pulmonary surfactant", composed mainly of phospholipids exists in the animal lungs. The pulmonary surfactant is mainly biosynthesized in and secreted from type II epithelial cells of the alveoli, and is known to be present as an internal lining of the wall of the whole respiratory tract including the alveolar region. It is known that pulmonary surfactant reduces the surface tension of the alveoli and prevents collapse of the alveoli. This action is of great physiological importance in that it helps to maintain respiratory function (L. G. Dobbs: Annual Rev. of Med., 40, 431–446, 1989). Infant respiratory distress syndrome which may lead to acute respiratory failure is caused by a deficiency of pulmonary surfactant. It is well documented that in adult respiratory distress syndrome decrease or dysfunction of pulmonary surfactant is also found. Moreover, Hallman et al. reported that in chronic diseases associated with respiratory failure, too, abnormality of pulmonary surfactant may occur (Journal of Clinical Investigation 70: 673–683, 1982).

Pulmonary surfactant plays an important role as a defense mechanism in the entire respiratory tract, as well as the anticollapse action. Thus, it is well documented that it prevents pulmonary edema and has preventive effects on bacterial or viral infection or on atmospheric pollutants and antigens which induce inflammation of the respiratory tract or asthmatic attacks. Moreover, pulmonary surfactant is known to play an important role in lubricating the respiratory lumen and expelling any foreign matter from the respiratory tract by activating mucociliary transport. As described above, pulmonary surfactant discharges various physiological functions in the respiratory system and, therefore, qualitative and quantitative changes of pulmonary surfactant seem to be related to the onset or aggravation of many respiratory diseases. Accordingly, the promotion of secretion of pulmonary surfactant may make it possible to treat or prevent various respiratory diseases, for example acute respiratory failure such as infant or adult respiratory distress syndrome, acute or chronic bronchitis, infectious disease, asthma and chronic respiratory failure.

Furthermore, it is thought that administration of pulmonary surfactant to a pregnant woman who may deliver an immature infant can prevent the onset of infant respiratory distress syndrome. Attempts have heretofore been made to utilize the naturally-occurring or genetically engineered pulmonary surfactant as such or a composition containing such pulmonary surfactant as the pulmonary surfactant (JP-B-1-13690, JP-A(PCT)-63-501792 and JP-A-2-53798, corresponding to U.S. Pat. No. 4,828,844, WO-8702037 and EP-A-0348967, respectively, the term "JP-A" as used herein means an "unexamined published Japanese patent application" and "JP-B" as used herein means an "examined Japanese patent publication") but as far as the activity to promote secretion of the endogenous pulmonary surfactant is concerned, ambroxol hydrochloride which is commercially available as an expectorant (Merck Index 11, pp. 62–63, 392 Ambroxol) is the only substance known to have such activity (Post et al.: Lung 161, 349–359, 1983).

Meanwhile, as a compound having the structure of 1,3- dihydro-2H-benzimidazol-2-one, a compound having a 3-dimethylaminopropyl group at the 1-position and no substituent on the benzene ring is described in Spectroscopy Letters, 5(9), 293 (1972) but the literature contains no description of its pharmacological activity. Aside from the above compound, the compound having a 2-diethylaminoethyl group at the 1-position and no substituent on the benzene ring and the compound having a 3-dimethylaminopropyl group at the 1-position and a chloro substituent at the 6-position are described in J. Chem. Soc., 314 (1960). In regard to pharmacological activity, however, it is only mentioned that 1-alkyl-2-oxobenzimidazoline compounds exhibit spinal reflex depressant activity, which is quite alien to the pharmacological activity according to the present invention, without giving specific pharmacological data.

A compound having a 2-piperidinoethyl group at the 1-position and no substituent on the benzene ring is also described in JP-A-62-252721. However, this compound is merely claimed to be useful as a peptic antiulcer agent. Thus, none of the literature mentioned above disclose any benzimidazolinone derivative having pulmonary surfactant secretion stimulatory activity as proposed by the present invention.

SUMMARY OF THE INVENTION

Under such state of the art, the present inventors carried out random screening of various synthetic compounds in an attempt to develop compounds having potent pulmonary surfactant secretion stimulatory activity and unexpectedly found that novel benzimidazolinone derivatives of the general formula (I) shown below or pharmaceutically acceptable salts thereof are superior in said activity than ambroxol. The present invention has been completed based on such finding. The present invention thus provides the benzimidazolinone derivatives of the general formula (I):

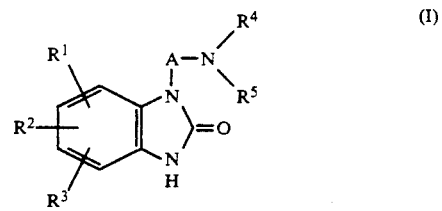

and salts thereof.

In the above formula, $R^1$, $R^2$ and $R^3$ are the same or different and each is a hydrogen or halogen atom or a lower alkyl, halo-lower alkyl, hydroxy-lower alkyl, hydroxy, lower alkoxy, aryloxy, cyano, carboxyl, lower alkoxycarbonyl, nitro, carbamoyl, or nitrogen-containing 5- or 6-membered heterocyclic group, A is an ethylene group which may optionally have at least one branch, $R^4$ and $R^5$ are the same or different and each is a lower alkyl group or $R^4$ and $R^5$ may be combined together with the adjacent nitrogen atom to form a pyrrolidinyl, piperidino or morpholino group provided that when

is a piperidino or diethylamino group, at least one of $R^1$, $R^2$ and $R^3$ is other than a hydrogen atom.

Among the compounds of this invention, those compounds in which $R^1$, $R^2$ and $R^3$ each is a hydrogen atom and

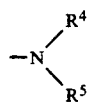

is a morpholino group literally fall within the broadly defined scope of compounds as described in the above-cited JP-A-62-252721, which contains no specific examples concerning said compounds. Therefore, these compounds are novel compounds which are synthesized for the first time by the present inventors.

DETAILED DESCRIPTION OF THE INVENTION

In the following, the compounds of this invention are described in detail.

As regards the definitions given herein relative to the general formulas shown above and hereinbelow, the term "lower", unless otherwise specified, means that the relevant group of a straight or branched carbon chain containing 1 to 6 carbon atoms.

Thus, the "lower alkyl group" specifically includes, among others, methyl, ethyl, propyl, isopropyl, butyl, isobutyl, sec-butyl, tert-butyl, pentyl (amyl), isopentyl, neopentyl, tert-pentyl, 1-methylbutyl, 2-methylbutyl, 1,2-dimethylpropyl, hexyl, isohexyl, 1-methylpenthyl, 2methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

As the "lower alkoxy group", there may be mentioned methoxy, ethoxy, propoxy, isopropoxy, butoxy, isobutoxy, secbutoxy, tert-butoxy, pentyloxy (amyloxy), isopentyloxy, tertpentyloxy, neopentyloxy, 2-methylbutoxy, 1,2-dimethylpropoxy, 1-ethylpropoxy, hexyloxy and so forth.

The "hydroxy-lower alkyl group" means a group derived from the above-mentioned "lower alkyl group" by substitution of one hydrogen atom thereof by a hydroxy group and, more specifically, includes, among others, hydroxymethyl, 2-hydroxyethyl, 3-hydroxypropyl, 2-hydroxypropyl, 2-hydroxy-1-methylethyl, 4-hydroxybutyl, 3-hydroxybutyl, 2-hydroxybutyl, 3-hydroxy-2-methylpropyl, 5-hydroxypentyl and 6-hydroxyhexyl.

The "halogen atom" is a fluorine, chlorine, bromine or iodine atom. The "halo-lower alkyl group" means a group derived from the above-mentioned "lower alkyl group" by substitution of any one to three hydrogen atoms with one to three atoms each of which independently is the "halogen atom" mentioned above, and typical examples are, when the halogen atom or atoms are represented by a fluorine atom or atoms, fluoromethyl, trifluoromethyl, 2-fluoroethyl, 3-fluoropropyl, 2-fluoro-1-methylethyl, 4-fluorobutyl, 3-fluoro-2-methylpropyl, 5-fluoropentyl, 4-fluoro-3-methylbutyl and 6-fluorohexyl, among others.

The "aryloxy group" includes, among others, phenoxy, 1-naphthyloxy, 2-naphthyloxy, etc.

The "acyl group" includes lower alkanoyl groups, such as formyl, acetyl, propionyl, butyryl, isobutyryl, valeryl, isovaleryl, pivaloyl, hexanoyl, etc.; aralkanoyl groups, such as benzylcarbonyl, 3-phenylpropanoyl, 2-phenylpropanoyl, 1-phenylpropanoyl, 4-phenylbutanoyl, 3-phenylbutanoyl, 2-phenylbutanoyl, 1-phenylbutanoyl, 2-methyl-3-phenylpropanoyl, 5-phenylpentanoyl, 4-phenylpentanoyl, 3-phenylpentanoyl, 2-phenylpentanoyl, 1-phenylpentanoyl, 3-methyl-4-phenylbutanoyl, 3-methyl-2-phenylbutanoyl, 6-phenylhexanoyl, 5-phenylhexanoyl, 4-phenylhexanoyl, 3-phenylhexanoyl, 2-phenylhexanoyl, 1-phenylhexanoyl, 4-methyl-5-phenylpentanoyl, 4-methyl-3-phenylhexanoyl, 4-methyl-2-phenylhexanoyl, etc.; and arylcarbonyl groups, such as benzoyl, naphthoyl, toluoyl, salicyloyl, anisoyl, veratroyl, protocatechuoyl, galloyl, etc.

The "lower alkoxycarbonyl group" is a group formed by the esterification of a straight or branched alcohol containing 1 to 6 carbon atoms and a carboxyl group and includes, among others, methoxycarbonyl, ethoxycarbonyl, propoxycarbonyl, isopropoxycarbonyl, butoxycarbonyl, isobutoxycarbonyl, secbutoxycarbonyl, tert-butoxycarbonyl, pentyloxycarbonyl, isopentyloxycarbonyl, neopentyloxycarbonyl, tertpentyloxycarbonyl and hexyloxycarbonyl.

The branch or branches of the "ethylene group which may optionally have at least one branch" preferably includes those typical examples of the above-mentioned "lower alkyl group" and accordingly said "ethylene group which may optionally have at least one branch" includes, as typical examples thereof, 1-methylethylene, 2-methylethylene, 1-ethylethylene, 2-ethylethylene, 1,1-dimethylethylene, 1,2-dimethylethylene, 2,2-dimethylethylene, 1-propylethylene, 2-propylethylene, 1-isopropylethylene, 2-isopropylethylene, 1-butylethylene, 2-butylethylene, 1-isobutylethylene, 2-isobutylethylene, 1-pentylethylene, 2-pentylethylene, 1-hexylethylene, 2-hexylethylene, etc.

The "nitrogen-containing 5- or 6-membered heterocyclic group" includes, among others, pyrrolyl, pyrrolidinyl, pyranyl, pyridyl, imidazolyl, imidazolinyl, pyrazolyl, pyrimidyl, pyrazinyl, and pyridazinyl.

The compounds (I) according to the present invention may form salts with acids, as the case may be. They may form salts with bases depending on the substituent or substituents. Such salts include addition salts with inorganic acids such as hydrochloric acid, hydrobromic acid, hydroiodic acid, sulfuric acid, nitric acid and phosphoric acid, and with organic acids such as formic acid, acetic acid, propionic acid, oxalic acid, malonic acid, succinic acid, fumaric acid, maleic acid, malic acid, tartaric acid, methanesulfonic acid and ethanesulfonic acid, addition salts with acidic amino acids such as aspartic acid and glutamic acid, salts with inorganic bases such as sodium, potassium, magnesium, calcium and aluminum, with organic bases such as methylamine, ethylamine and ethanolamine, and with basic amino acids such as lysine and ornithine, and the ammonium salt.

The compound (I) of the present invention may assume a tautomeric structure due to its imidazol-2-one moiety and may also exist as optical isomers depending on kinds of substituent groups. These various stereoisomers are also included within the scope of the present invention in either isolated form or mixture form thereof.

Among the compounds (I) according to the present invention, the preferred compounds are compounds wherein $R^1$, $R^2$, $R^3$ may be the same or different and each is a hydrogen atom, a halogen atom, or a lower alkoxy group and compounds wherein

is a dimethylamino group or pyrrolidinyl group.

By taking advantage of characteristics of its skeletal structure and substituent groups, the compound (I) of the present invention can be synthesized by a variety of processes. Representative examples of such processes are described below.

Process 1

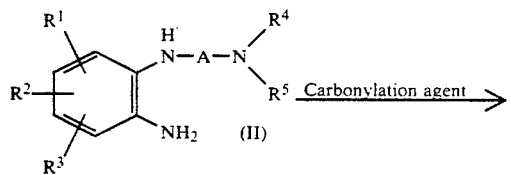

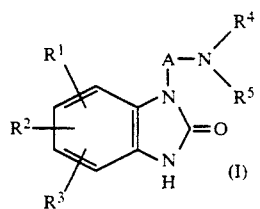

In the above reaction formula, $R^1$, $R^2$, $R^3$, $R^4$, $R^5$ and A have the same meanings as respectively defined hereinbefore.

The compound (I) of the present invention can be synthesized by reacting a compound of general formula (II) with a carbonylation agent in the presence or absence of a base.

The carbonylation agent mentioned above includes, among others, haloformic esters such as ethyl chloroformate etc. diethyl carbonate, urea, diphenyl carbonate, N,N'-disuccinimidyl carbonate, N,N'-carbonyldiimidazole and so on. When a haloformic ester is used as the carbonylation agent, this process is performed as follows. Thus, in an inert solvent such as benzene, toluene, xylene, tetrahydrofuran, diethyl ether, N,N-dimethylformamide, chloroform, dichloromethane or ethyl acetate, the compound (II) is reacted with 2 or more molar equivalents of the carbonylation agent in the presence of a base, such as an inorganic base, e.g. sodium hydroxide, potassium hydroxide, etc., or an organic base, e.g. triethylamine, trimethylamine, pyridine, picoline, N,N-dimethylaniline, etc. at room temperature or under warming, preferably at the reflux temperature, to give an intermediate of the formula (III)

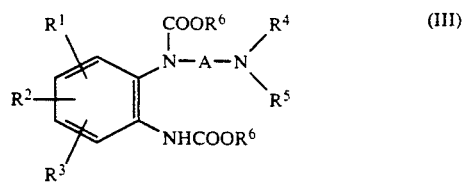

wherein $R^1$, $R^2$, $R^3$, $R^4$, $R^5$ and A have the same meanings as respectively defined hereinbefore; $R^6$ is a lower alkyl group.

This intermediate is isolated and, then, cyclized in the presence of a base such as an alkali metal alkoxide, e.g. sodium ethoxide, in an inert organic solvent such as an alcohol, e.g. methanol, ethanol, isopropyl alcohol, methoxyethanol (methylcellosolve), ethoxyethanol (ethylcellosolve), etc., at room temperature or under warming, preferably at the reflux temperature, to give the compound (I) of the present invention.

In this connection, when such a haloformic ester is used in an approximately equimolar amount to the starting compound, the compound of the following formula (IV) is obtained stably as the intermediate.

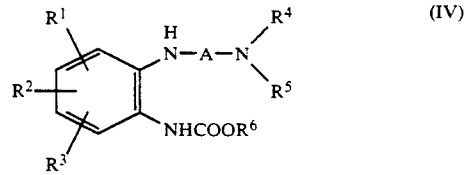

wherein $R^1$, $R^2$, $R^3$, $R^4$, $R^5$, $R^6$ and A have the same meanings as respectively defined hereinbefore. This intermediate (IV) is isolated and, where necessary, subjected to a further reaction and, again, a reaction with the carbonylation agent to give compound (III) which, after isolation or without isolation, is heated on reflux in the presence of a base to give the compound (I) of the present invention.

On the other hand, the process using urea, diphenyl carbonate, N,N'-disuccinimidyl carbonate or N,N'-carbonyldiimidazole as the carbonylation agent is performed as follows. Thus, this reaction is conducted in the absence of a base in an organic solvent similar to the one mentioned above at room temperature, under warming, or at the reflux temperature, whereby the compound (I) of the present invention is obtained in one step.

Incidentally, the starting compound (II) can be easily made available by reducing the corresponding nitro compound and this corresponding nitro compound can be prepared by reacting the corresponding halide with a substituted ethylenediamine or reacting the corresponding nitroaniline with a substituted aminoethyl halide.

Process 2

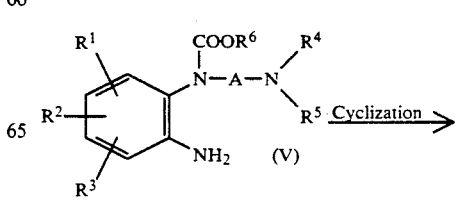

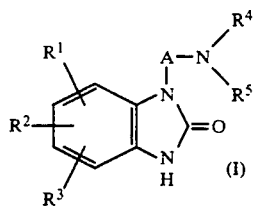

wherein $R^1$, $R^2$, $R^3$, $R^4$, $R^5$, $R^6$ and A have the same meanings as respectively defined hereinbefore.

The compound (I) of the present invention can also be synthesized by cyclizing a phyenylenediamine compound having a primary amino group (V).

This reaction is advantageously carried out in the presence of an acid, e.g. hydrochloric acid or sulfuric acid, in an inert organic solvent such as an alcohol, e.g. methanol, ethanol, isopropyl alcohol, methoxyethanol(-methylcellsolve), ethoxyethanol(ethylcellosolve), etc., at the reflux temperature.

Alternatively, as in Process 1, this starting compound (V) is first reacted with a carbonylation agent to give compound (III) which, after isolation or without isolation, is cyclized into the compound (I) of the present invention.

The starting compound (V) can be easily made available by reacting the corresponding nitro compound with a carbonylation agent and reducing the reaction product.

Process 3

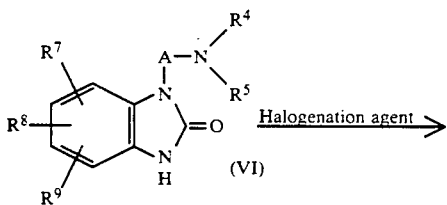

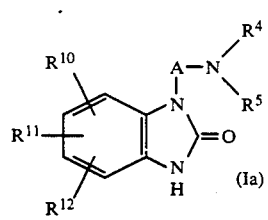

In the above reaction formula, A, $R^4$ and $R^5$ have the same meanings as respectively defined hereinbefore; $R^7$, $R^8$ and $R^9$ are such that one of them is a hydrogen atom with the other two being either the same or different and each representing hydrogen, halogen, lower alkyl, halo-lower alkyl, lower alkoxy, aryloxy, acyl, cyano, carboxyl, lower alkoxycarbonyl, nitro, carbamoyl, or nitrogen-containing 5- or 6-membered heterocyclic group; $R^{10}$, $R^{11}$ and $R^{12}$ are such that one of them is a halogen atom with the other two being either the same or different and each representing hydrogen, halogen, lower alkyl, halo-lower alkyl, lower alkoxy, aryloxy, acyl, cyano, carboxyl, lower alkoxycarbonyl, nitro, carbamoyl, or nitrogen-containing 5- or 6-membered heterocyclic group. Among compounds of the present invention, compounds substituted by 1 to 3 halogen atoms (Ia) can be synthesized by halogenating a compound of general formula (VI).

The halogenation agent useful for this purpose includes, among others, chlorine, bromine, iodine, benzyltrimethylammonium tribromide, phenyltrimethylammonium tribromide, copper (II) halides, e.g. copper (II) chloride etc., dioxane dibromide, pyridinium hydrobromide perbromide, pyrrolidone hydrotribromide and so on.

This process is advantageously conducted by reacting compound (VI) with a stoichiometric amount, viz. 1 to 3 molar equivalents, or an excess, of the halogenation agent in an inert solvent, e.g. an organic solvent such as dichloromethane, dichloroethane, chloroform, carbon tetrachloride, ether, tetrahydrofuran, dioxane, acetic acid, N,N-dimethylformamide, methanol, ethanol, water, or a mixture thereof, where necessary in the presence of a reagent assisting in halogenation, such as calcium carbonate, zinc chloride or the like, and, in certain instances, with the aid of a catalyst such as an alkali halide or a hydrogen halide, at room temperature or under warming.

Process 4

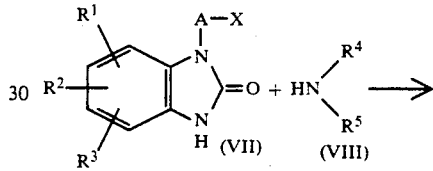

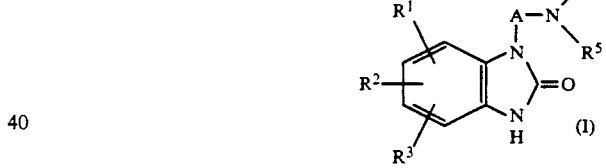

In the above reaction formula, $R^1$, $R^2$, $R^3$, $R^4$, $R^5$ and A have the same meanings as respectively defined hereinbefore; X is a halogen atom or an organic sulfonate residue.

In the above formula, the halogen atom X may for example be iodine, bromine or chlorine and the organic sulfonate residue includes alkanesulfonate residues such as methanesulfonyloxy etc. and aromatic sulfonate residues such as benzenesulfonyloxy, toluenesulfonyloxy (particularly p-toluenesulfonyloxy) and so on.

The compound (I) of the present invention can also be synthesized by reacting a compound of general formula (VII) with an amine of general formula (VIII). This process is advantageously performed by reacting compound (VII) with a stoichiometric amount or an excess of compound (VIII) in an inert solvent, e.g. an organic solvent such as an alcohol methanol, ethanol, isopropyl alcohol, methoxyethanol (emthylcellosolve), ethoxyethanol (ethylcellosolve), etc., bis(2-methoxyethyl)ether (diglyme), benzene, toluene, xylene or the like, preferably in the presence of a base such as trimethylamine, triethylamine, diisopropylethylamine, N,N-dimethylaniline, pyridine, picoline, lutidine, etc. at room temperature, under warming or at the reflux temperature.

Process 5

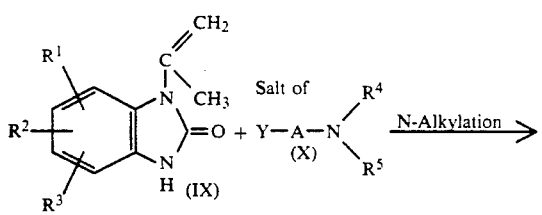

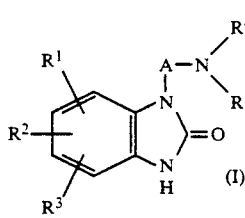

In the above reaction formula, $R^1$, $R^2$, $R^3$, $R^4$, $R^5$ and A have the same meanings as respectively defined hereinbefore; Y is a halogen atom.

The compound (I) of the present invention can also be synthesized by reacting a 1-(2-propenyl)-substituted benzimidazolinone (IX) with an aminoalkyl halide salt (X).

This process is advantageously performed by reacting compound (IX) with a stoichiometric amount or an excess of compound (X) in an organic solvent such as an alcohol, e.g. methanol, ethanol, isopropyl alcohol, etc., N,N-dimethylformamide, dimethyl sulfoxide, tetrahydrofuran or the like, preferably in the presence of a base such as an alkali metal alkoxide, e.g. sodium methoxide, sodium ethoxide, etc., sodium hydride, potassium hydride, lithium diisopropylamide, etc., at room temperature, under warming or at the reflux temperature. Then, the propenyl group is removed in the presence of hydrochloric acid, sulfuric acid or the like to give the compound (I).

Process 6

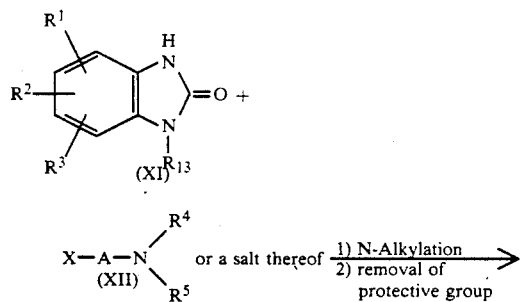

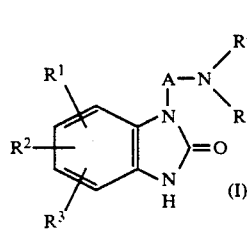

In the above reaction formula, $R^1$, $R^2$, $R^3$, $R^4$, $R^5$, X and A have the same meanings as respectively defined hereinbefore; $R^{13}$ is an amino-protecting group. The amino-protecting group $R^{13}$ includes, among others, benzyl type protective groups such as benzyl, benzhydryl, trityl, 4-methoxybenzyl, etc., acyl type protective groups such as formul, acetyl, propionyl, etc., and urethane type protective groups such as t-butoxycarbonyl etc.

The compound (I) of the present invention can also be synthesized by reacting a protected benzimidazol-2-one derivative of general formula (XI) with a halide or sulfonate of general formula (XII) and removing the protective group.

This process is advantageously performed by reacting compound (XI) with a stoichiometric amount or an excess of compound (XII) or its salt in an inert solvent such as an organic solvent, e.g. alcohols such as methanol, ethanol, isopropyl alcohol, methoxyethanol (methylcellosolve), ethoxyethanol (ethylcellosolve), etc., bis(2-methoxyethyl)ether (diglyme), benzene, toluene, xylene, etc., preferably in the presence of a base such as sodium hydride, potassium hydride, sodium hydroxide, trimethylamine, triethylamine, diisopropylethylamine, N,N-dimethylaniline, pyridine, picoline, lutidine, etc., at room temperature or under warming, preferably at the reflux temperature and, then, removing the protective group.

The method of removal of the protective group depends on the type of protective group. By way of illustration, benzyl type protective groups can be easily eliminated by reduction or oxidation and acyl type and urethane type protective groups can be easily eliminated by hydrolysis under acidic or basic conditions.

Process 7

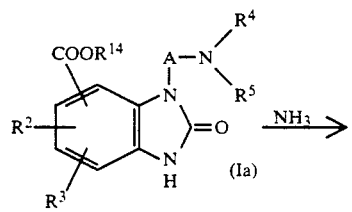

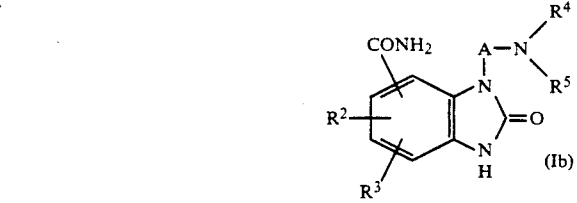

In the above reaction formula, $R^2$, $r^3$, $R^4$, $R^5$ and A have the same meanings as respectively defined hereinbefore; $R^{14}$ is a lower alkyl group.

Among compounds of the present invention, a compound having at least one carbamoyl group as represented by general formula (Ib) can be synthesized by ammonolysis, namely by treating the corresponding lower alkoxycarbonyl-substituted compound (Ia) with ammonia.

For this ammonolysis, liquid ammonia is advantageously employed and the reaction can also be carried out in a solvent such as methanol, ethanol or the like. The use of water and glycol which hasten the reaction is advantageous. It is also advantageous, for promoting the reaction, to employ ammonium chloride, sodium methoxide, sodium amide, sodium hydride or butyllithium as a catalyst.

Though the reaction temperature varies with other conditions, the reaction can generally be conducted with advantage at room temperature or under warming.

Process 8

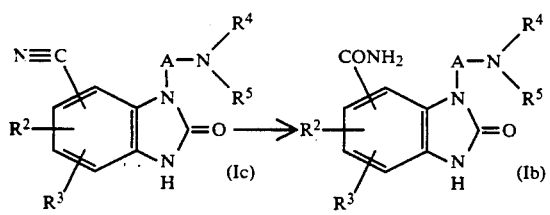

In the above reaction formula, $R^2$, $R^3$, $R^4$, $R^5$ and A have the meanings respectively defined hereinbefore.

Among compounds of the present invention, a compound having at least one carbamoyl group as represented by general formula (Ib) can be synthesized by hydrolyzing the corresponding cyano-substituted compound (Ic).

This reaction is advantageously conducted in an inert solvent such as methanol, ethanol, isopropyl alcohol, tertbutanol, methoxyethanol (methylcellosolve), ethoxyethanol (ethylcellosolve), water or the like in the presence of a base such as sodium hydroxide or potassium hydroxide at room temperature or under warming; or in the solvent such as tertbutanol or water in the presence of an acid such as hydrochloric acid or sulfuric acid at room temperature or under warming. The reaction can also be conducted advantageously using a base, such as sodium hydroxide, and hydrogen peroxide in a solvent such as alcohols, dichloromethane, chloroform and so on. In this case, the reaction is preferably carried out in the presence of a phase transfer catalyst such as tetrabutylammonium hydrogen sulfate and so on.

Process 9

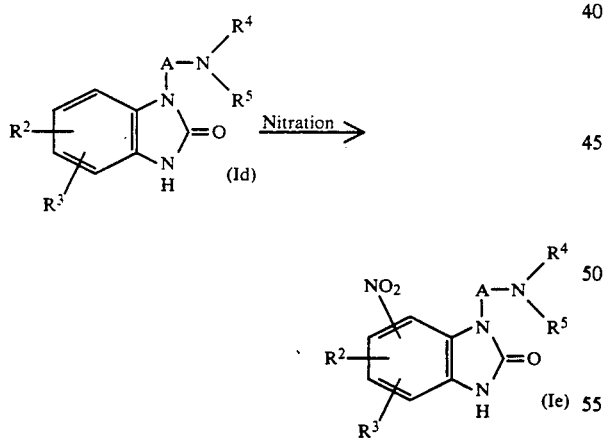

In the above reaction formula, $R^2$, $R^3$, $R^4$, $R^5$ and A are as defined before.

Among the formula (Ie) compounds, compounds having a nitro group(s) can be produced by nitrating the corresponding starting compounds (Id).

The reaction may be conducted under various conditions, but, it can be preferably conducted by reacting the formula (Id) compound with a nitration agent such as a mixed acid of sulfuric acid and fuming nitric acid, a mixed solution of sulfuric acid and nitric acid salt (e.g. potassium nitrate), anhydride of nitric acid and acetic acid, etc., in no solvent or in an organic solvent such as dichloromethane, nitromethane, acetic acid, sulfolane, etc., under cooling below 20° C., preferably below 10° C., and then at room temperature after exothermic condition is over.

Process 10

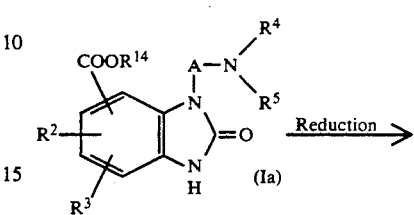

In the above reaction formula, $R^2$, $R^3$, $R^4$, $R^5$, $R^{14}$ and A are as defined before.

The hydroxymethyl compounds of the formula (If) may be produced by using the corresponding starting compound (the lower alkoxy carbonyl substituted compound of the formula (Ia)) by reducing this starting compound.

The reduction may be performed in a solvent such as tetrahydrofuran (which does not take part in the reducing reaction) by applying chemical reduction using metal hydride such as lithium aluminum hydride, sodium boron hydride, etc. or sodium metal in liquid ammonia, or by applying catalytic reduction using a catalyst such as rhenium oxide. It is preferred to conduct the reduction in usual manner, and it is preferred that a group susceptive to reduction reaction such as a nitro group is not present, if such group is present, only a lower alkoxycarbonyl group may be reduced selectively, or at the same time, a nitro group may be also reduced.

The reaction product obtained in any of the above processes is isolated and purified in the free form as such or as a salt. The salt can be produced by subjecting the free compound to the usual salt forming reaction.

The isolation and purification can be carried out by the usual chemical procedures such as extraction, concentration, distillation, crystallization, filtration, recrystallization, chromatography and so on.

The compound (I) of this invention and salts thereof have stimulating effect on the secretion of pulmonary surfactant and are useful in the treatment and prevention of diseases in which the pulmonary surfactant is deficient or dysfunctioned, for example respiratory diseases such as infant respiratory distress syndrome (IRDS), adult respiratory distress syndrome (ARDS), pulmonary edema, acute or chronic respiratory failure, acute or chronic bronchitis, infections, asthma, etc.

The stimulating effect of the compound of this invention on the secretion of pulmonary surfactant has been confirmed by the method described below.

The stimulatory effect of the compound of the present invention on pulmonary surfactant secretion In the experiment, male Hartley guinea pigs weighing 300-350 g were used.

Methods 50 mg/kg of the test compound was intraperitoneally administered to guinea pigs once. Three hours later, the animals were anesthetized with 100 mg/kg of pentobarbital sodium and sacrificed by bleeding from the abdominal aorta and vena cava. Then, bronchoalveolar lavage with 10 ml/kg of ice-cooled physiological saline was performed twice. The combined bronchoalveolar lavage fluid was centrifuged at 1,000 rpm for 10 minutes at 4° C.

From the supernatant of bronchoalveolar lavage fluid, the lipid was extracted in accordance with the method of Folch et al. (Journal of Biological Chemistry, 226, 497-502, 1957). The characteristic component of pulmonary surfactant, i.e., disaturated phosphatidylcholine was extracted by the method of Gilfillan et al. (Journal of Lipid Research, 24, 1651- 1656, 1983). The disaturated phosphatidylcholine was assayed with Nescoat PL Kit-K (Nippon Shoji Co., Ltd.) and the percent increase compared to a control group was determined (M. Takayama, et al.: Clin. Chim. Acta, 79, 93-98, 1977).

The results are shown in Table 1.

TABLE 1

| Compound Example No. | Pharmacological activity: % increase of disaturated phosphatidylcholine (DSPC) compared to control values (number of animals) |
|---|---|
| 3(5) | 27.9 ± 6.2 (3)* |
| 4(3) | 32.3 ± 7.0 (3)* |
| 11(4) | 37.8 ± 13.2 (3)* |
| 12(5) | 27.4 ± 4.9 (6)* |
| 19(4) | 33.1 ± 8.3 (5)* |
| Compound A (Note 1) | −9.3 |
| Compound B (Note 2) | −20.7 |

*Significantly different from control values ($p < 0.05$).
Note 1: 1,3-Dihydro-1-(3-dimethylaminopropyl)-2H-benzimidazol-2-one
Note 2: 1,3-Dihydro-1-(2-diethylaminoethyl)-2H-benzimidazol-2-one It is apparent from the above table that the compounds of the present invention potently stimulate pulmonary surfactant secretion and that compound A or B, structurally quite close to the compounds of the invention, do not stimulate secretion of pulmonary surfactant but rather tend to decrease the secretion.

Pharmaceutical compositions containing one or more of the compound (I) and/or their salt of the invention can be manufactured using the carriers, excipients and additives commonly employed in the pharmaceutical field and provided in such dosage forms as tablets, powders, fine granules, granules, capsules, pills, oral liquids (including syrups), injections, drip infusions, inhalants, suppositories, liquids for percutaneous administration, ointments, transdermal therapeutic systems (e.g. buccal preparations), transmucosal therapeutic systems (e.g. nasal liquids) and so on. These preparations are administered orally or parenterally, or via maternal bodies.

The clinical dosage of the compound of the invention depends on the disease, symptom, body weight, age and sex of the patient to be treated, the route of administration and other factors.

Taking infant respiratory distress syndrome as an example, the preferred intravenous dosage, for instance, is 1 to 500 mg/day for direct administration to neonates and 1 to 5,000 mg, preferably 1 to 2,000 mg, for administration via maternal bodies. In other diseases, the adult daily dose is 1 to 2,000 mg, preferably 1 to 500 mg for oral administration, or 1 to 2,000 mg, preferably 1 to 500 mg for parenteral administration, to be administered in a single dose or in 2 to 4 divided doses in either case.

The following examples are further illustrative of the invention. It should be noted that while some of the starting compounds, are novel a series of production processes for these compounds are also included in the examples.

In the examples, "mp" stands for melting point, "Analysis" for elemental analysis, and "NMR" for nuclear magnetic resonance spectrum.

Unless otherwise noted, the ratios used hereinbefore and hereinafter are by volume.

EXAMPLE 1

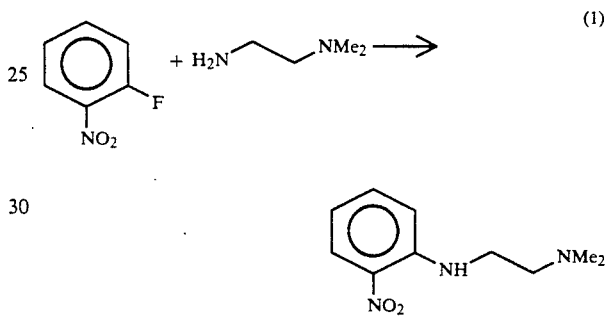

(1)

To a solution of 2-fluoronitrobenzene (103.0 g) in 2-propanol (350 ml) was added a solution of N,N-dimethylethylenediamine (128.8 g) in 2-propanol (165 ml) dropwise over a period of 30 minutes. The reaction mixture was heated at 50° C. for 4 hours and at 70° C. for 3 hours. The reaction mixture was concentrated under reduced pressure and the residue was dissolved in ethyl acetate, washed with water (×3) and saturated aqueous sodium chloride solution in the order mentioned and dried over anhydrous sodium sulfate. The solution was concentrated under reduced pressure to give 149.2 g of N-(2-nitrophenyl)-N',N'-dimethylethylenediamine.

Mass spectrum (m/z): 210 (MH+).

NMR (CDCl$_3$) δ: 2.31 (6H, s), 2.50-2.75 (2H, m), 3.25-3.45 (2H, m), 6.53-6.88 (2H, m), 7.33-7.53 (1H, m), 8.71 (1H, dd, J=1.5 and 8.5 Hz), 8.30 (1H, br s).

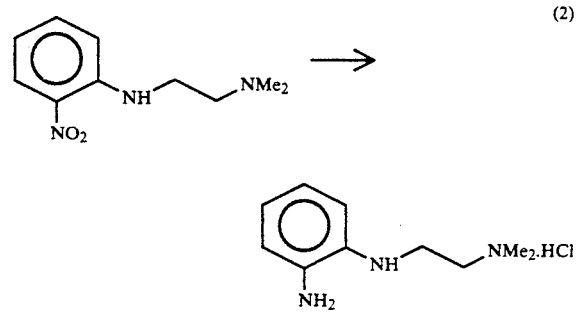

(2)

To a solution of N-(2-nitrophenyl)-N',N'-dimethylethylenediamine (149.2 g) in methanol (1500 ml) were added concentrated hydrochloric acid (60 ml) and 10% palladium-on-carbon (15 g). The reaction mixture was stirred under a hydrogen atmosphere at atmospheric pressure for 5.5 hours. The reaction mixture was then filtered and concentrated under reduced pressure to give 149.2 g of N-(2-aminophenyl)-N',N'-dimethylethylenediamine hydrochloride.

| Analysis (for C₁₀H₁₈N₃Cl) | | | | |
|---|---|---|---|---|
| | C (%) | H (%) | N (%) | Cl (%) |
| Calcd.: | 55.68 | 8.41 | 19.48 | 16.43 |
| Found: | 55.57 | 8.40 | 19.54 | 16.12 |

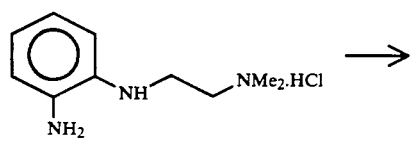
(3)

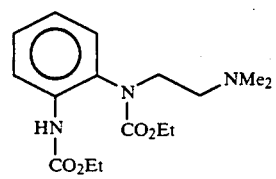

In 1N aqueous solution of sodium hydroxide (120 ml) was dissolved N-(2-aminophenyl)-N',N'-dimethylethylenediamine hydrochloride (10.0 g) and the free amine was extracted with chloroform (100 ml). The organic layer was dried over anhydrous sodium sulfate and concentrated to half the initial volume. To this solution was added ethyl chloroformate (10.1 g) dropwise, followed by addition of triethylamine (4.5 g). The reaction mixture was stirred at room temperature for 1 hour, was successively washed with 1N aqueous sodium hydroxide solution and saturated aqueous sodium chloride solution and dried over anhydrous sodium sulfate. The solvent was then distilled off under reduced pressure and the residue was purified by silica gel chromatography (eluent: chloroform:methanol=50:1) to give 14.6 g of N-(2-ethoxycarbonylaminophenyl)-N-ethoxycarbonyl-N',N'-dimethylethylenediamine.

Mass spectrum (m/z): 324 (MH+).

NMR (CDCl₃) δ: 0.90–1.45 (6H, m), 2.00–3.25 (2H, m), 2.27 (6H, s), 3.75–4.70 (6H, m), 6.90–7.45 (3H, m), 7.90–8.05 (1H, m), 10.60 (1H, br s).

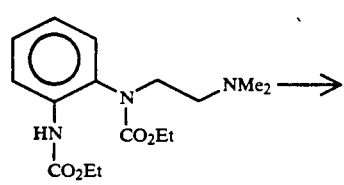
(4)

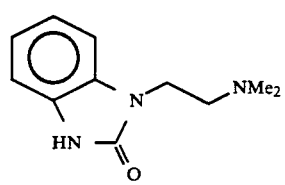

In ethanol (100 ml) was dissolved sodium metal (0.70 g) followed by addition of a solution of N-(2-ethoxycarbonylaminophenyl)-N-ethoxycarbonyl-N',N'-dimethylethylenediamine (4.88 g) in ethanol (20 ml). The reaction mixture was refluxed for 16 hours and was concentrated under reduced pressure. The residue was diluted with chloroform and the insoluble matter was filtered off. The solvent was then distilled off and the residue was purified by silica gel chromatography (eluent:chloroform:methanol=10:1) to give 2.69 g of 1,3-dihydro-1-(2-dimethylaminoethyl)-2H-benzimidazol-2-one.

mp: 106°–107.5° C.

Mass spectrum (m/z): 205 (M+).

NMR (CDCl₃) δ: 2.32 (6H, s), 2.64 (2H, t, J=7 Hz), 4.00 (2H, t, J=7 Hz), 6.94–7.12 (4H, m), 9.96 (1H, br s).

(5)

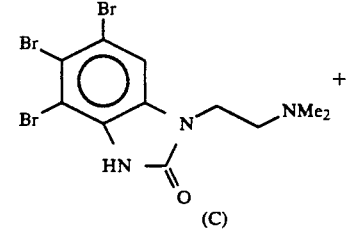

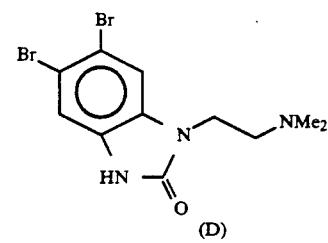

To a solution of 1,3-dihydro-1-(2-dimethylaminoethyl)-2H-benzimidazol-2-one (0.63 g) in acetic acid (20 ml) were added zinc chloride (1.33 g) and benzyltrimethylammonium tribromide (2.64 g). The reaction mixture was stirred at 70° C. for 24 hours, after which the solvent was distilled off under reduced pressure. To the residue was added a saturated aqueous sodium hydrogen carbonate solution and the product was extracted with ethyl acetate. The organic layer was washed with saturated aqueous sodium chloride solution and dried over anhydrous sodium sulfate. The solvent was distilled off under reduced pressure and the residue was purified by silica gel chromatography (eluent: chloroform:methanol=15:1) to give 0.31 g of 1,3-dihydro-1-(2-dimethylaminoethyl)-4,5,6-tribromo-2H-benzimidazol-2-one (Compound C) and 0.45 g of 5,6-dibromo-1,3-dihydro-1-(2-dimethylaminoethyl)-2H-benzimidazol-2-one (Compound D).

Compound C

Mass spectrum (m/z): 440, 442, 444, 446 (MH+).

NMR (CDCl$_3$) δ: 2.36 (6H, s), 2.72 (2H, t, J=7 Hz), 3.92 (2H, t, J=7 Hz), 7.16 (1H, s).

Compound D

Mass spectrum (m/z) 362, 364, 366 (MH+).

NMR (CDCl$_3$) δ: 2.29 (6H, s), 2.59 (2H, t, J=7 Hz), 3.89 (2H, t, J=7 Hz), 7.24 (1H, s), 7.25 (1H, s), 10.90 (1H, br s).

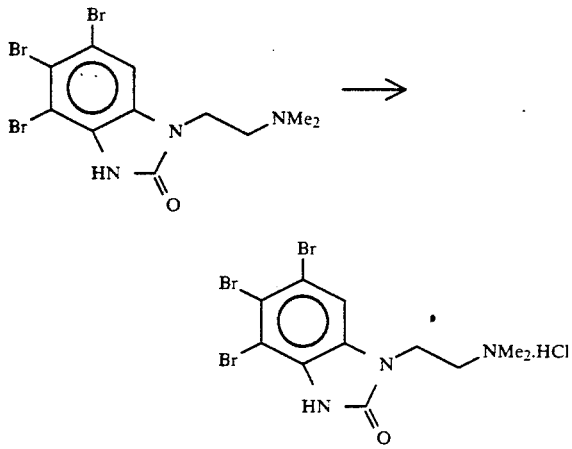

To a solution of 1,3-dihydro-1-(2-dimethylaminoethyl)-4,5,6-tribromo-2H-benzimidazol-2-one (270 mg) in ethanol (5 ml)/ethyl acetate (40 ml) was added 4N hydrogen chloride in dioxane dropwise with stirring. The separated crystals were collected by suction and dried to give 260 mg of 1,3-dihydro-1-(2-dimethylaminoethyl)-4,5,6-tribromo-2H-benzimidazol-2-one hydrochloride.

mp: 268°–273° C.

| Analysis (for C$_{11}$H$_{13}$N$_3$OBr$_3$Cl) | | | | |
|---|---|---|---|---|
| C (%) | H (%) | N (%) | Br (%) | Cl (%) |
| Calcd.: 27.62 | 2.74 | 8.78 | 50.11 | 7.41 |
| Found: 27.61 | 2.65 | 8.51 | 49.85 | 7.16 |

The following compound was prepared in generally the same manner as (6).

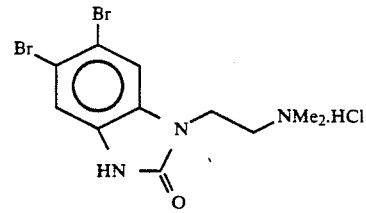

5,6-Dibromo-1,3-dihydro-1-(2-dimethylaminoethyl)-2H-benzimidazol-2-one hydrochloride.

Starting compound: 5,6-Dibromo-1,3-dihydro-1-(2-dimethylaminoethyl)-2H-benzimidazol-2-one.

mp: 249°–254° C.

| Analysis (for C$_{11}$H$_{14}$N$_3$OBr$_2$Cl.0.7H$_2$O) | | | | |
|---|---|---|---|---|
| C (%) | H (%) | N (%) | Br (%) | Cl (%) |
| Calcd.: 32.06 | 3.77 | 10.20 | 38.78 | 8.60 |
| Found: 31.98 | 3.42 | 9.91 | 39.06 | 8.31 |

EXAMPLE 2

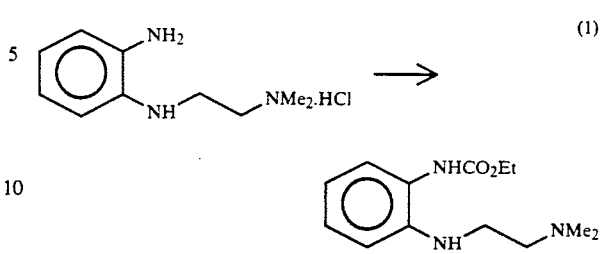

In 1N aqueous sodium hydroxide solution 120 ml) was dissolved N-(2-aminophenyl)-N',N'-dimethylethylenediamine hydrochloride (1.80 g) and the free amine was extracted with chloroform (50 ml). The organic layer was dried over anhydrous sodium sulfate and concentrated to half the initial volume. To this solution was added ethyl chloroformate (0.90 g) dropwise. The reaction mixture was stirred at room temperature for 1 hour, successively washed with 1N aqueous sodium hydroxide solution and saturated aqueous sodium chloride solution and dried over anhydrous sodium sulfate. The solvent was then distilled off under reduced pressure and the residue was purified by silica gel chromatography (eluent:chloroform:methanol=10:1) to give 0.96 g of N-(2-ethoxycarbonylaminophenyl)-N',N'-dimethylethylenediamine.

Mass spectrum (m/z): 252 (MH+).

NMR (CDCl$_3$) δ: 1.28 (3H, t, J=7 Hz), 2.22 (6H, s), 2.44–2.56 (2H, m), 3.04–3.24 (2H, m), 4.00–4.24 (1H, m), 4.20 (2H, q, J=7 Hz), 6.64–7.48 (5H, m),

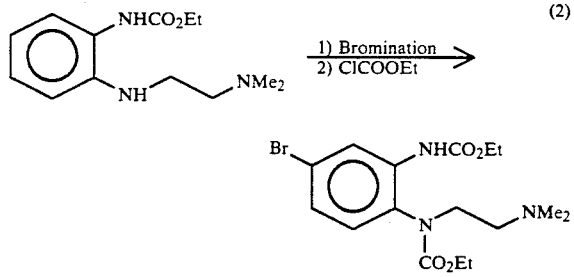

To a solution of N-(2-ethoxycarbonylaminophenyl)-N',N'-dimethylethylenediamine (0.94 g) in methanol (20 ml) and dichloromethane (30 ml) were added calcium carbonate (0.40 g) and benzyltrimethylammonium tribromide (1.46 g). The reaction mixture was stirred at room temperature for 1.5 hours. The insoluble matter was then filtered off and the solvent was distilled off under reduced pressure. The residue was diluted with 1N aqueous sodium hydroxide solution and extracted with ethyl acetate. The organic layer was dried over anhydrous sodium sulfate, the solvent was distilled off, and the residue was dissolved in chloroform (30 ml). To the solution was added ethyl chloroformate (0.53 g) dropwise, and the reaction mixture was stirred at room temperature for 5 hours. The reaction mixture was successively washed with 1N aqueous sodium hydroxide solution and saturated aqueous sodium chloride solution and dried over anhydrous sodium sulfate. The solvent was distilled off under reduced pressure and the residue was purified by silica gel chromatography (eluent:chloroform:methanol=50:1) to give 0.95 g of N-(4- bromo-2-ethoxycarbonylaminophenyl)-N-ethoxycarbonyl-N',N'-dimethylethylenediamine.

Mass spectrum (m/z): 402, 404 (MH+).

NMR (CDCl₃) δ: 1.01–1.34 (6H, m), 2.27 (6H, s), 2.37–2.57 (2H, m), 2.89–3.11 (1H, m), 3.98–4.65 (6H, m), 6.91 (1H, d, J=12 Hz), 7.15 (1H, dd, J=2 and 12 Hz), 8.23 (1H, d, J=2 Hz),.

(3) The following compound was prepared in generally the same manner as Example 1(4).

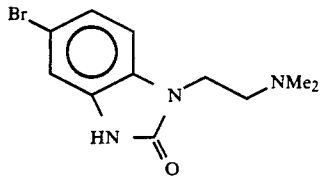

5-Bromo-1,3-dihydro-1-(2-dimethylaminoethyl)-2H-benzimidazol-2-one.

Starting compound: N-(4-Bromo-2-ethoxycarbonylaminophenyl)-N-ethoxycarbonyl-N',N'-dimethylethylenediamine.

Mass spectrum (m/z): 284, 286 (MH+).

NMR (CDCl₃) δ: 2.34 (6H, s), 2.65 (2H, t, J=7 Hz), 3.96 (2H, t, J=7 Hz), 6.84 (1H, d, J=9 Hz), 7.04–7.20 (2H, m), 10.31 (1H, br s).

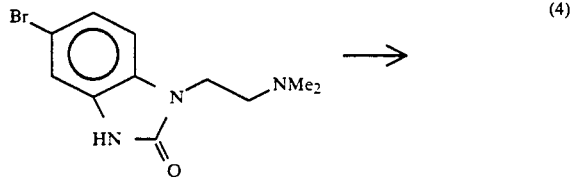

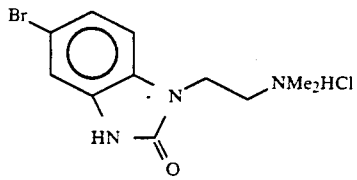

To a solution of 5-bromo-1,3-dihydro-1-(2-dimethylaminoethyl)-2H-benzimidazol-2-one (510 mg) in ethanol (5 ml) and diethyl ether (50 ml) was added 4N hydrogen chloride in dioxane dropwise with stirring. The separated crystals were collected by suction and dried to give 490 mg of 5-bromo-1,3-dihydro-1-(2-dimethylaminoethyl)-2H-benzimidazol-2-one hydrochloride.

mp: 254°–261° C.

Analysis (for C₁₁H₁₅N₃OBrCl) C(%) H(%) N(%) Br(%) Calcd.: 41.21 4.72 13.11 24.92 Found: 41.58 4.74 12.92 25.01

EXAMPLE 3

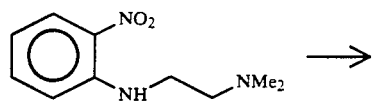

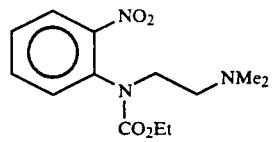

To a solution of N-(2-nitrophenyl-N',N'-dimethylethylenediamine (1.20 g) in chloroform (25 ml) was added ethyl chloroformate (0.64 g) dropwise. The reaction mixture was stirred at room temperature for 5 hours, washed with 1N aqueous sodium hydroxide solution and saturated aqueous sodium chloride solution in turn and dried over anhydrous sodium sulfate. The solvent was then distilled off under reduced pressure and the residue was purified by silica gel chromatography (eluent:chloroform:methanol=10:1) to give 1.10 g of N-(2-nitrophenyl)-N-ethoxycarbonyl-N',N'-dimethylethylenediamine.

Mass spectrum (m/z): 282 (MH+).

NMR (CDCl₃) δ: 1.08 (3H, t, J=7 Hz), 2.16 (6H, s), 2.52 (2H, t, J=7 Hz), 3.64–4.32 (4H, m), 7.28–7.70 (3H, m), 7.88–8.00 (1H, m),

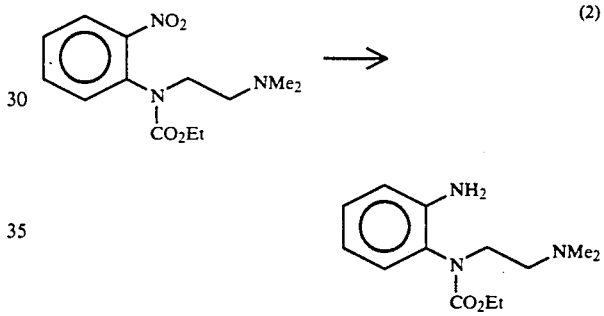

To a solution of N-ethoxycarbonyl-N-(2-nitrophenyl)-N',N'-dimethylethylenediamine (1.08 g) in methanol (25 ml) was added 10% palladium-on-carbon (0.1 g). The mixture was stirred under a hydrogen atmosphere at atmospheric pressure for 30 minutes, and filtered. The solvent was distilled off under reduced pressure to give 0.93 g of N-(2-aminophenyl)-N-ethoxycarbonyl-N',N'-dimethylethylenediamine.

Mass spectrum (m/z): 252 (MH+).

NMR (CDCl₃) δ: 1.11–1.31 (3H, m), 2.34 (6H, s), 2.46–2.76 (2H, m), 3.06–3.48 (2H, m), 3.93–4.57 (4H, m), 6.60–7.50 (4H, m).

(3) The following compound was prepared in generally the same manner as Example 2(2).

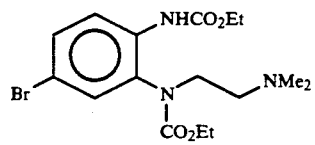

N-(5-Bromo-2-ethoxycarbonylaminophenyl)-N-ethoxycarbonyl-N',N'-dimethylethylenediamine.

Starting compound: N-(2-Aminophenyl)-N-ethoxycarbonyl-N',N'-dimethylethylenediamine.

Mass spectrum (m/z): 402, 404 (MH+).

NMR (CDCl₃) δ: 1.04–1.10 (3H, m), 1.24–1.32 (3H, m), 2.26 (6H, s), 2.50–2.62 (1H, m), 3.00–3.16 (1H, m), 3.84–4.04 (1H, m), 4.08–4.30 (4H, m), 4.36–4.56 (1H, m), 7.20–7.32 (1H, m), 7.36–7.44 (1H, m), 7.90 (1H, d, J=10 Hz), 10.70 (1H, s).

(4) The following compound was prepared in generally the same manner as Example 1(4).

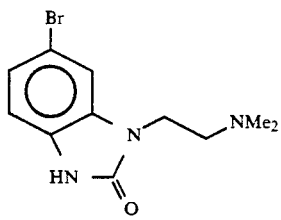

6-Bromo-1,3-dihydro-1-(2-dimethylaminoethyl)-2H-benzimidazol-2-one.

Starting compound: N-(5-Bromo-2-ethoxycarbonylaminophenyl)-N-ethoxycarbonyl-N',N'-dimethylethylenediamine.

Mass spectrum (m/z): 284, 286 (MH+).

NMR (CDCl$_3$) δ: 2.36 (6H, s), 2.66 (2H, t, J=7 Hz), 3.96 (2H, t, J=7 Hz), 6.90 (1H, d, J=10 Hz), 7.10–7.20 (2H, m), 10.20 (1H, s).

(5) The following compound was prepared in generally the same manner as Example 2(4).

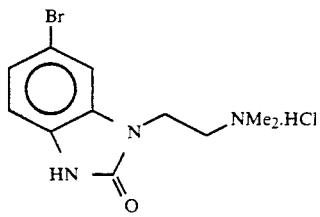

6-Bromo-1,3-dihydro-1-(2-dimethylaminoethyl)-2H-benzimidazol-2-one hydrochloride.

Starting compound: 6-Bromo-1,3-dihydro-1-(2-dimethylaminoethyl)-2H-benzimidazol-2-one.

mp: 252°–258° C.

| | Analysis (for C$_{11}$H$_{15}$N$_3$OBrCl) | | | |
|---|---|---|---|---|
| | C (%) | H (%) | N (%) | Cl (%) |
| Calcd.: | 41.21 | 4.72 | 13.11 | 11.06 |
| Found: | 41.38 | 4.73 | 12.95 | 10.94 |

EXAMPLE 4

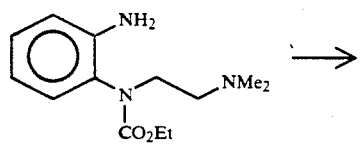

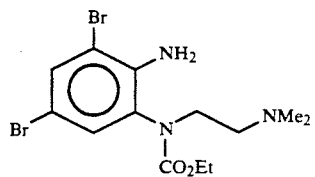

To a solution of N-(2-aminophenyl)-N-ethoxycarbonyl-N',N'-dimethylethylenediamine (1.60 g) in methanol (20 ml) and dichloromethane (30 ml) were added calcium carbonate (1.29 g) and benzyltrimethylammonium tribromide (5.05 g), and the reaction mixture was stirred at room temperature for 24 hours. The insoluble matter was filtered off and the solvent was distilled off under reduced pressure. To the residue were added 5% aqueous sodium hydrogen sulfite solution and 1N aqueous sodium hydroxide solution to make the solution alkaline and extracted with ethyl acetate. The organic layer was washed with saturated aqueous sodium chloride solution and dried over anhydrous sodium sulfate. The solvent was distilled off under reduced pressure and the residue was purified by silica gel chromatography (eluent: chloroform:methanol=30:1) to give 0.87 g of N-(2-amino-3,5-dibromophenyl)-N-ethoxycarbonyl-N',N'-dimethylethylenediamine.

Mass spectrum (m/z): 408, 410, 412 (MH+).

NMR (CDCl$_3$)

δ: 1.04–1.40 (3H, m), 2.16 (6H, s), 2.30–2.40 (2H, m), 3.04–3.24 (1H, m), 4.00–4.40 (3H, m), 5.36 (2H, br s), 7.09 (1H, d, J=2 Hz), 7.50 (1H, d, J=2 Hz).

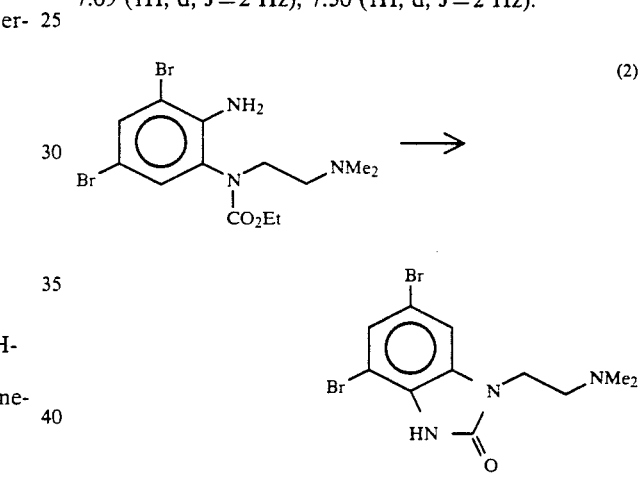

In ethanol (21 ml) and concentrated hydrochloric acid (7 ml) was dissolved N-(2-amino-3,5-dibromophenyl)-N-ethoxycarbonyl-N',N'-dimethylethylenediamine (0.85 g) and the solution was refluxed for 2 hours. The reaction mixture was concentrated under reduced pressure and the residue was diluted with water. The solution was alkalized with sodium hydroxide and extracted with ethyl acetate. The organic layer was washed with saturated aqueous sodium chloride solution and dried over anhydrous sodium sulfate. The solvent was distilled off under reduced pressure and the residue was purified by silica gel chromatography (eluent: chloroform:methanol=10:1) to give 0.59 g of 4,6-dibromo-1,3-dihydro-1-(2-dimethylaminoethyl)-2H-benzimidazol-2-one.

Mass spectrum (m/z): 362, 364, 366 (MH+).

NMR (CDCl$_3$)

δ: 2.38 (6H, s), 2.71 (2H, t, J=7 Hz), 7.05 (1H, d, J=1.5 Hz), 7.23 (1H, d, J=1.5 Hz), 10.08 (1H, br s).

(3) The following compound was prepared in generally the same manner as Example 1(6).

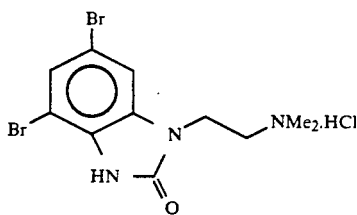

4,6-Dibromo-1,3-dihydro-1-(2-dimethylaminoethyl)-2H-benzimidazol-2-one hydrochloride.

Starting compound: 4,6-Dibromo-1,3-dihydro-1-(2-dimethylaminoethyl)-2H-benzimidazol-2-one.

mp: 261°–268° C. (decompn.).

| Analysis (for $C_{11}H_{14}N_3OBr_2Cl.0.2H_2O$) | | | | |
|---|---|---|---|---|
| C (%) | H (%) | N (%) | Br (%) | Cl (%) |
| Calcd.: 32.78 | 3.60 | 10.42 | 39.64 | 8.79 |
| Found: 32.79 | 3.40 | 10.40 | 39.54 | 8.56 |

EXAMPLE 5

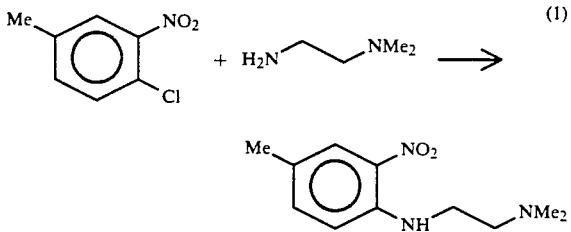

A mixed solution of 4-chloro-3-nitrotoluene (1.30 g) and N,N-dimethylethylenediamine (1.34 g) in 1-propanol (20 ml) was refluxed for 24 hours and the solvent was distilled off under reduced pressure. The residue was dissolved in ethyl acetate and the solution was successively washed with water (×2) and saturated aqueous sodium chloride solution and dried over anhydrous sodium sulfate. The solvent was then distilled off under reduced pressure and the residue was purified by silica gel chromatography (eluent: chloroform:methanol=30:1) to give 0.19 g of N-(4-methyl-2-nitrophenyl)-N',N'-dimethylethylenediamine.

Mass spectrum (m/z): 224 (MH+).

NMR (CDCl₃δ: 2.26 (3H, s), 2.30 (3H, s), 2.62 (2H, t, J=7 Hz), 3.25–3.44 (2H, m), 6.75 (1H, d, J=9 Hz), 7.27 (1H, dd, J=2 and 9 Hz), 7.97 (1H, d, J=2 Hz), 8.17 (1H, br s).

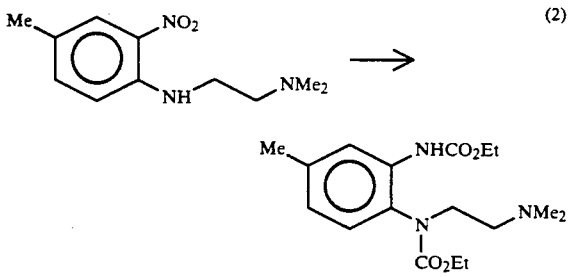

A mixture of N-(4-methyl-2-nitrophenyl)-N',N'-dimethylethylenediamine (0.47 g), concentrated hydrochloric acid (0.2 ml) and 10% palladium-on-carbon (0.05 g) in methanol (20 ml) was stirred under a hydrogen atmosphere at atmospheric pressure for 2 hours. The catalyst was filtered off and the filtrate was concentrated under reduced pressure. The residue was dissolved in chloroform (30 ml) followed by dropwise addition of triethylamine (0.66 g) and ethyl chloroformate (0.54 g) in turn. The reaction mixture was stirred at room temperature for 1.5 hours and was successively washed with 1N aqueous sodium hydroxide solution and saturated aqueous sodium chloride solution and dried over anhydrous sodium sulfate. The solvent was distilled off under reduced pressure and the residue was purified by silica gel chromatography (eluent: chloroform:methanol=30:1) to give 0.62 g of N-(2-ethoxycarbonylamino-4-methylphenyl)-N-ethoxycarbonyl-N',N'-dimethylethylenediamine.

Mass spectrum (m/z): 338 (MH+).

NMR (CDCl₃) δ: 1.00–1.40 (6H, m), 2.26 (6H, s), 2.34 (3H, s), 2.30–2.60 (2H, m), 2.92–3.20 (1H, m), 3.80–4.60 (5H, m), 6.76–7.00 (2H, m), 7.72–8.00 (1H, m).

(3) The following compound was prepared in generally the same manner as Example 1(4).

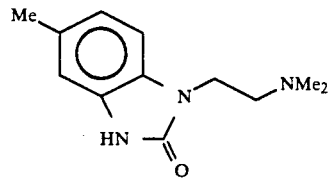

1,3-Dihydro-1-(2-dimethylaminoethyl)-5-methyl-2H-benzimidazol-2-one.

Starting compound: N-(2-Ethoxycarbonylamino-4-methyl)-N-ethoxycarbonyl-N',N'-dimethylethylenediamine.

Mass spectrum (m/z): 220 (MH+).

NMR (CDCl₃) δ: 2.34 (6H, s), 2.36 (3H, s), 2.66 (2H, t,J=7 Hz), 3.99 (2H, t, J=7 Hz), 6.88 (3H, s), 9.67 (1H, br s).

(4) The following compound was prepared in generally the same manner as Example 2(4).

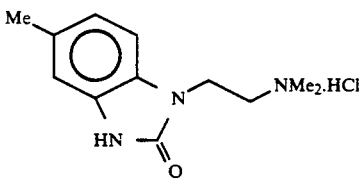

1,3-Dihydro-1-(2-dimethylaminoethyl)-5-methyl-2H-benzimidazol-2-one hydrochloride.

Starting compound: 1,3-Dihydro-1-(2-dimethylaminoethyl)-5-methyl-2H-benzimidazol-2-one.

mp: 230°–240° C.

| Analysis (for $C_{12}H_{18}N_3OCl.0.3H_2O$) | | | |
|---|---|---|---|
| C (%) | H (%) | N (%) | Cl (%) |
| Calcd.: 55.19 | 7.18 | 16.09 | 13.58 |
| Found: 55.15 | 7.10 | 15.79 | 13.57 |

EXAMPLE 6

(1) The following compound was prepared in generally the same manner as Example 5(1).

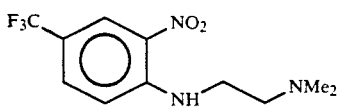

N-(2-Nitro-4-trifluoromethylphenyl)-N',N'-dimethylethylenediamine.

Starting compound: 4-Chloro-3-nitrobenzotrifluoride. Mass spectrum (m/z): 278 (MH+).

NMR (CDCl$_3$) δ: 2.31 (6H, s), 2.65 (2H, t, J=6 Hz), 3.29–3.47 (2H, m), 6.91 (1H, d, J=11 Hz), 7.61 (1H, dd, J=2 and 11 Hz), 8.46 (1H, d, J=2 Hz), 8.61 (1H, br s).

(2) The following compound was prepared in generally the same manner as Example 5(2).

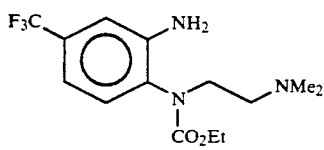

N-(2-Amino-4-trifluoromethylphenyl)-N-ethoxycarbonyl-N',N'-dimethylethylenediamine.

Starting compound: N-(2-Nitro-4-trifluoromethylphenyl)-N',N'-dimethylethylenediamine.

Mass spectrum (m/z): 320 (MH+).

NMR (CDCl$_3$) δ: 1.04–1.40 (3H, m), 2.26 (6H, s), 2.16–2.44 (2H, m), 3.04–3.36 (1H, m), 4.00–4.44 (3H, m), 4.90 (2H, br s), 6.84–7.10 (3H, m).

(3) The following compound was prepared in generally the same manner as Example 4(2).

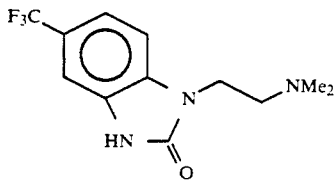

1,3-Dihydro-1-(2-dimethylaminoethyl)-5-trifluoromethyl-2H-benzimidazol-2-one.

Starting compound: N-(2-Amino-4-trifluoromethylphenyl)-N-ethoxycarbonyl-N',N'-dimethylethylenediamine.

Mass spectrum (m/z): 274 (MH+).

NMR (CDCl$_3$) δ: 2.34 (6H, s), 2.68 (2H, t, J=7 Hz), 4.01 (2H, t, J=7 Hz), 7.00–7.40 (3H, m), 10.76 (1H, br s).

(40 The following compound was prepared in generally the same manner as Example 2(4).

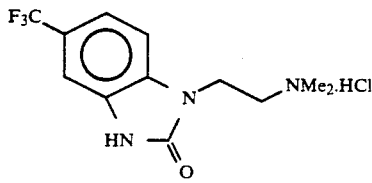

1,3-Dihydro-1-(2-dimethylaminoethyl)-5-trifluoromethyl-2H-benzimidazol-2-one hydrochloride.

Starting compound 1,3-Dihydro-1-(2-dimethylaminoethyl)-5-trifluoromethyl-2H-benzimidazol-2-one.

mp: 215°–218° C.

| Analysis (for C$_{12}$H$_{15}$N$_3$OF$_3$Cl.H$_2$O) | | | | |
|---|---|---|---|---|
| | C (%) | H (%) | N (%) | Cl (%) |
| Calcd.: | 43.98 | 5.23 | 12.82 | 10.82 |
| Found: | 43.45 | 4.64 | 12.42 | 10.49 |

EXAMPLE 7

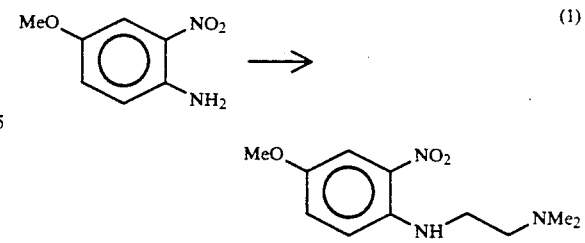

(1)

To a solution of 4-methoxy-2-nitroaniline (2.08 g) in dichloromethane (40 ml) was added trifluoroacetic anhydride (10 ml) and the mixture was stirred at room temperature for 1 hour. The reaction mixture was concentrated under reduced pressure and the residue was dissolved in acetone (40 ml) followed by addition of 2-chloroethyldimethylamine hydrochloride (1.82 g) and anhydrous potassium carbonate (3.40 g). The mixture was refluxed for 6 hours, and after addition of water (40 ml), refluxed for another 2 hours. The reaction mixture was concentrated under reduced pressure to half the initial volume, diluted with 1N aqueous sodium hydroxide solution and extracted with ethyl acetate. The organic layer was washed with saturated aqueous solution of sodium chloride and dried over anhydrous magnesium sulfate. The solvent was then distilled off under reduced pressure and the residue was purified by silica gel chromatography eluent:chloroform:methanol=15:1) to give 1.28 g of N-(4-methoxy-2-nitrophenyl)-N',N'-dimethylethylenediamine.

Mass spectrum (m/z): 240 (MH+).

NMR (CDCl$_3$) δ: 2.30 (6H, s), 2.62 (2H, t, J=6 Hz), 3.25–3.45 (2H, m), 3.79 (3H, s), 6.81 (1H, d, J=11 Hz), 7.15 (1H, dd, J=2, 11 Hz), 7.62 (1H, d, J=2 Hz), 8.21 (1H, br s).

(2) The following compound was prepared in generally the same manner as Example 5(2).

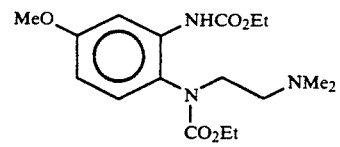

N-(2-Ethoxycarbonylamino-4-methoxyphenyl)-N-ethoxycarbonyl-N',N'-dimethylethylenediamine.

Starting compound: N-(4-Methoxy-2-nitrophenyl)-N',N'-dimethylethylenediamine.

Mass spectrum (m/z) 354 (MH+).

NMR (CDCl$_3$) δ: 1.08 (3H, t, J=7 Hz), 1.28 (3H, t, J=7 Hz), 2.28 (6H, s), 2.20–2.40 (1H, m), 2.46–2.60 (1H, m), 2.96–3.10 (1H, m), 3.84 (3H, s), 3.86–4.04 (1H, m), 4.08–4.28 (3H, m), 4.36–4.52 (1H, m), 6.58 (1H, dd, J=2 and 10 Hz), 6.96 (1H, d, J=10 Hz), 7.66 (1H, br s), 10.70 (1H, br s).

(3) The following compound was prepared in generally the same manner as Example 1(4).

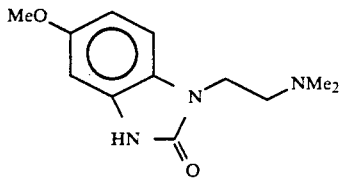

1,3-Dihydro-1-(2-dimethylaminoethyl)-5-methoxy-2H-benzimidazol-2-one.

Starting compound: N-(2-Ethoxycarbonylamino-4-methoxyphenyl)-N-ethoxycarbonyl-N',N'-dimethylethylenediamine.

Mass spectrum (m/z) 236 (MH+).

NMR (CDCl₃) δ: 2.32 (6H, s), 2.64 (2H, t, J=7 Hz), 3.76 (3H, s), 3.96 (2H, t, J=7 Hz), 6.52–6.96 (3H, m), 10.60 (1H, br s).

(4) The following compound was prepared in generally the same manner as Example 2(4).

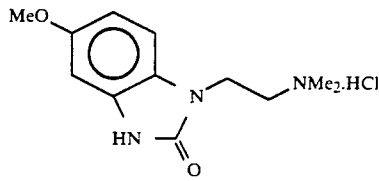

1,3-Dihydro-1-(2-dimethylaminoethyl)-5-methoxy-2H-benzimidazol-2-one hydrochloride.

Starting compound: 1,3-Dihydro-1-(2-dimethylaminoethyl)-5-methoxy-2H-benzimidazol-2-one.
mp: 253°–257° C.

| Analysis (for C₁₂H₁₈N₃O₂Cl.0.2H₂O) | | | | |
|---|---|---|---|---|
| | C (%) | H (%) | N (%) | Cl (%) |
| Calcd.: | 52.35 | 6.74 | 15.26 | 12.88 |
| Found: | 52.57 | 6.79 | 15.05 | 12.47 |

(5)

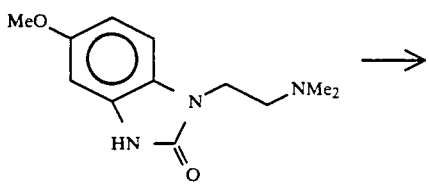

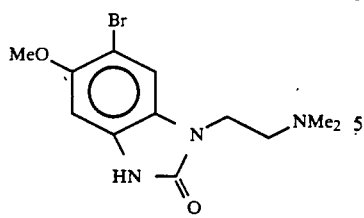

To a solution of 1,3-dihydro-1-(2-dimethylaminoethyl)-5-methoxy-2H-benzimidazol-2-one (0.28 g) in methanol (10 ml) and dichloromethane (15 ml) were added calcium carbonate (0.25 g) and benzyltrimethylammonium tribromide (0.49 g). The reaction mixture was stirred at room temperature for 16 hours and the insoluble matter was filtered off. The solvent was then distilled off under reduced pressure and the residue was diluted with 1N aqueous sodium hydroxide solution and extracted with ethyl acetate. The organic layer was washed with saturated aqueous sodium chloride solution and dried over anhydrous sodium sulfate. The solvent was then distilled off under reduced pressure and the residue was purified by silica gel chromatography (eluent: chloroform:methanol=10:1) to give 0.35 g of 6-bromo-1,3-dihydro-1-(2-dimethylaminoethyl)-5-methoxy-2H-benzimidazol-2-one.

Mass spectrum (m/z): 314 (MH+).

NMR (CDCl₃) δ: 2.35 (6H, s), 2.67 (2H, t, J=7 Hz), 3.86 (3H, s), 3.95 (2H, t, J=7 Hz), 6.67 (1H, s), 7.17 (1H, s), 10.89 (1H, br s).

(6) The following compound was prepared in generally the same manner as Example 1(6).

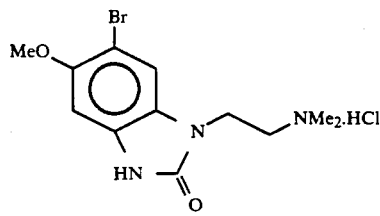

6-Bromo-1,3-dihydro-1-(2-dimethylaminoethyl)-5-methoxy-2H-benzimidazol-2-one hydrochloride.

Starting compound: 6-Bromo-1,3-dihydro-1-(2-dimethylaminoethyl)-5-methoxy-2H-benzimidazol-2-one
mp: 238°–244° C. (decompn.).

| Analysis (for C₁₂H₁₇N₃O₂BrCl.H₂O) | | | | | |
|---|---|---|---|---|---|
| | C (%) | H (%) | N (%) | Br (%) | Cl (%) |
| Calcd.: | 39.10 | 5.19 | 11.40 | 21.67 | 9.62 |
| Found: | 39.28 | 4.93 | 11.34 | 21.82 | 9.59 |

EXAMPLE 8

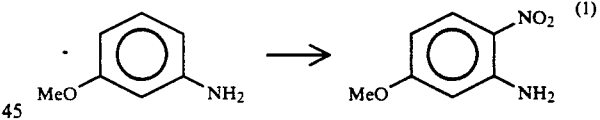

(1)

A solution of 3-methoxyaniline (2.21 g) in acetic acid (3 ml) and acetic anhydride (10 ml) was stirred at room temperature for 1 hour. The solution was cooled to 5° C. and 60% nitric acid (1 ml) was added dropwise with stirring. When the cooling bath was removed, whereupon the solution temperature rose to 60° C. The solution was allowed to cool down to room temperature, poured into ice-water (100 ml) and neutralized with sodium hydroxide. The separated crystals were collected by suction and washed with water. To the crystals was added 4N hydrochloric acid (45 ml) and the mixture was refluxed for 2 hours. The reaction mixture was alkalized with sodium hydroxide and extracted with ethyl acetate. The organic layer was washed with saturated aqueous sodium chloride solution and dried over anhydrous magnesium sulfate. The solvent was distilled off under reduced pressure and the residue was purified by silica gel chromatography (eluent: chloroform) to give 0.67 g of 5-methoxy-2-nitroaniline.

Mass spectrum (m/z): 168 (M+).

NMR (CDCl₃) δ: 3.90 (3H, s), 4.32 (2H, br s), 6.12–6.28 (2H, m), 7.94 (1H, d, J=10 Hz).

(2) The following compound was prepared in generally the same manner as Example 7(1).

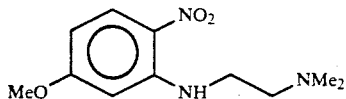

N-(5-Methoxy-2-nitrophenyl)-N',N'-dimethylethylenediamine.

Starting compound: 5-Methoxy-2-nitroaniline.

Mass spectrum (m/z): 240 (MH+).

NMR (CDCl$_3$) δ: 2.31 (6H, s), 2.64 (2H, t, J=6 Hz), 3.23-3.43 (2H, m), 3.86 (3H, s), 6.13-6.29 (2H, m), 8.10 (1H, d, J=11 Hz), 8.51 (1H, br s).

(3) The following compound was prepared in generally the same manner as Example 5(2).

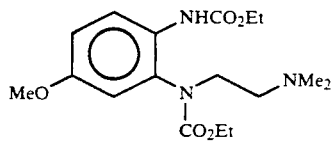

N-(2-Ethoxycarbonylamino-5-methoxy]-N-ethoxycarbonyl-N',N'-dimethylethylenediamine.

Starting compound: N-(5-Methoxy-2-nitrophenyl)-N',N'-dimethylethylenediamine.

Mass spectrum (m/z): 354 (MH+).

NMR (CDCl$_3$) δ: 0.96-1.40 (6H, m), 2.24 (6H, s), 2.10-2.72 (2H, m), 2.88-3.24 (1H, m), 3.76 (3H, s), 3.80-4.60 (5H, m), 6.60 (1H, d, J=3 Hz), 6.82 (1H, dd, J=3 and 10 Hz), 7.80 (1H, d, J=10 Hz), 10.37 (1H, br s), (4) The following compound was prepared in generally the same manner as Example 1(4).

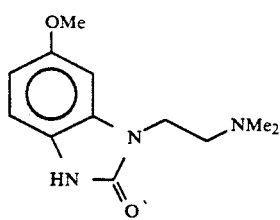

1,3-Dihydro-1-(2-dimethylaminoethyl)-6-methoxy-2H-benzimidazol-2-one.

Starting compound: N-(2-Ethoxycarbonylamino-5-methoxy)-N-ethoxycarbonyl-N',N'-dimethylethylenediamine.

Mass spectrum (m/z): 236 (MH+).

NMR (CDCl$_3$) δ: 2.34 (6H, s), 2.65 (2H, t, J=7 Hz), 3.82 (3H, s), 3.97 (2H, t, J=7 Hz), 6.54-6.67 (2H, m), 6.95 (1H, d, J=9 Hz), 9.01 (1H, br s).

(5) The following compound was prepared in generally the same manner as Example 2(4).

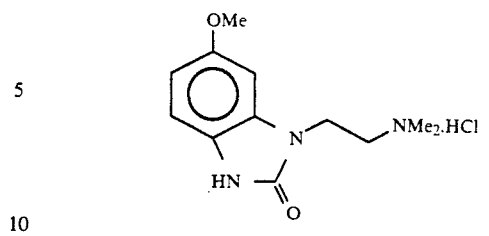

1,3-Dihydro-1-(2-dimethylaminoethyl)-6-methoxy-2H-]benzimidazol-2-one hydrochloride.

Starting compound: 1,3-Dihydro-1-(2-dimethylaminoethyl)-6-methoxy-2H-benzimidazol-2-one.

mp: 217°-220° C.

| Analysis (for C$_{12}$H$_{18}$N$_3$O$_2$Cl.0.2H$_2$O) | | | | |
|---|---|---|---|---|
| | C (%) | H (%) | N (%) | Cl (%) |
| Calcd.: | 52.35 | 6.74 | 15.26 | 12.88 |
| Found: | 52.40 | 6.57 | 15.17 | 13.07 |

EXAMPLE 9

1) The following compound was prepared in generally the same manner as Example 8(1).

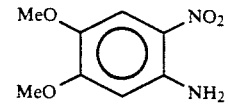

4,5-Dimethoxy-2-nitroaniline.

Starting compound: 3,4-Dimethoxyaniline.

Mass spectrum (m/z): 198 (M+).

NMR (CDCl$_3$) δ: 3.86 (3H, s), 3.91 (3H, s), 6.17 (1H, s), 6.10-6.40 (2H, m), 7.53 (1H, s).

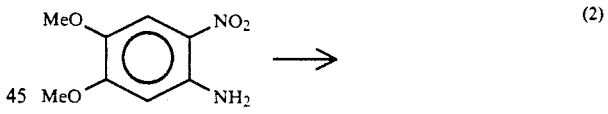 (2)

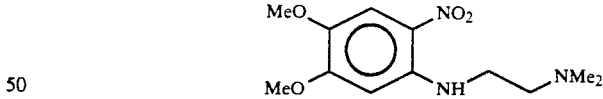

To a solution of 4,5-dimethoxy-2-nitroaniline (0.81 g) and 2-chloroethyldimethylamine hydrochloride (0.73 g) in N,N-dimethylformamide (20 ml) was added sodium hydride (0.36 g) in small portions with ice-cooling and the reaction mixture was heated at 60° C. for 2 hours. The reaction mixture was diluted with 1N aqueous sodium hydroxide solution and extracted with ethyl acetate. The organic layer was successively washed with water and saturated aqueous sodium chloride solution and dried over anhydrous sodium sulfate. The solvent was then distilled off under reduced pressure and the residue was purified by silica gel chromatography (eluent:chloroform:methanol=15:1) to give 0.77 g of N-(4,5-dimethoxy-2-nitrophenyl)-N',N'-dimethylethylenediamine.

Mass spectrum (m/z): 270 (MH+).

NMR (CDCl₃) δ: 2.32 (6H, s), 2.65 (2H, t, J=6 Hz), 3.28–3.47 (2H, m), 3.86 (3H, s), 3.96 (3H, s), 6.18 (1H, s), 7.61 (1H, s), 8.69 (1H, br s).

(3) The following compound was prepared in generally the same manner as Example 5(2).

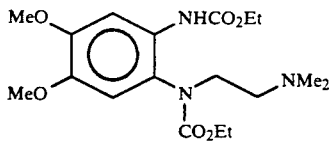

N-(4,5-Dimethoxy-2-ethoxycarbonylaminophenyl)-N-ethoxy-carbonyl-N',N'-dimethylethylenediamine.

Starting compound: N-(4,5-Dimethoxy-2-nitrophenyl)-N',N'-dimethylethylenediamine Mass spectrum (m/z): 384 (MH⁺).

NMR (CDCl₃) δ: 1.00–1.40 (6H, m), 2.24 (6H, s), 2.20–2.70 (2H, m), 2.92–3.10 (1H, m), 3.80 (3H, s), 3.88 (3H, s), 3.70–4.60 (5H, m), 6.52 (1H, s), 7.60 (1H, br s), 10.53 (1H, br s).

(4) The following compound was prepared in generally the same manner as Example 1(4).

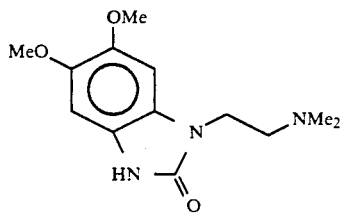

1,3-Dihydro-5,6-dimethoxy-1-(2-dimethylaminoethyl)-2H-benzimidazol-2-one.

Starting compound: N-(4,5-Dimethoxy-2-ethoxycarbonylaminophenyl)-N-ethoxycarbonyl-N',N'-dimethylethylenediamine.

Mass spectrum (m/z): 266 (MH⁺).

NMR (CDCl₃) δ: 2.36 (6H, s), 2.68 (2H, t, J=8 Hz), 3.88 (3H, s), 3.92 (3H, s), 4.00 (2H, t, J=8 Hz), 6.72 (1H, s), 6.80 (1H, s), 10.50 (1H, br s).

(5) The following compound was prepared in generally the same manner as Example 2(4).

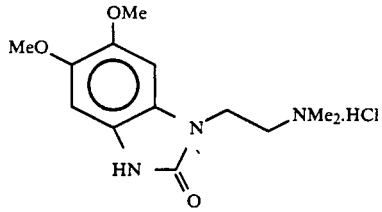

1,3-Dihydro-5,6-dimethoxy-1-(2-dimethylaminoethyl)-2H-benzimidazol-2-one hydrochloride.

Starting compound: 1,3-Dihydro-5,6-dimethoxy-1-(2-dimethylaminoethyl)-2H-benzimidazol-2-one.

mp: 242°–248° C.

| Analysis (for C₁₃H₂₀N₃O₃Cl.0.3H₂O) | | | | |
|---|---|---|---|---|
| | C (%) | H (%) | N (%) | Cl (%) |
| Calcd.: | 50.83 | 6.76 | 13.68 | 11.54 |
| Found: | 50.66 | 6.98 | 13.67 | 11.51 |

EXAMPLE 10

(1) The following compound was prepared in generally the same manner as Example 8(1).

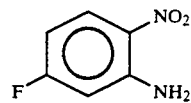

5-Fluoro-2-nitroaniline.
Starting compound: 3-Fluoroaniline.
Mass spectrum (m/z): 156 (M⁺).
NMR (CDCl₃) δ: 6.20 (2H, br s), 6.32–6.55 (2H, m), 8.08–8.25 (1H, m).

(2) The following compound was prepared in generally the same manner as Example 9(2).

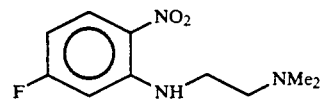

N-(5-Fluoro-2-nitrophenyl)-N',N'-dimethylethylenediamine.
Starting compound: 5-Fluoro-2-nitroaniline.
Mass spectrum (m/z): 228 (MH⁺).
NMR (CDCl₃) δ: 2.31 (6H, s), 2.63 (2H, t, J=6 Hz), 3.20–3.39 (2H, m), 6.24–6.60 (2H, m), 8.02–8.30 (1H, m), 8.50 (1H, br s).

(3)

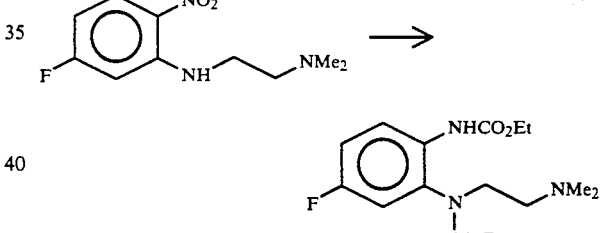

To a solution of N-(5-fluoro-2-nitrophenyl)-N',N'-dimethylethylenediamine (0.55 g) in methanol (20 ml) were added concentrated hydrochloric acid (0.2 ml) and platinum oxide (0.06 g) and the reaction mixture was stirred under a hydrogen atmosphere at atmospheric pressure for 30 minutes. The reaction mixture was then filtered and the solvent was distilled off under reduced pressure. To the residue was added chloroform (25 ml) followed by dropwise addition of triethylamine (0.97 g) and ethyl chloroformate (0.60 g) in turn. After being stirred at room temperature for 2 hours, the reaction mixture was successively washed with 1N aqueous sodium hydroxide solution and saturated aqueous sodium chloride solution and dried over anhydrous sodium sulfate. The solvent was then distilled off under reduced pressure and the residue was purified by silica gel chromatography (eluent:chloroform:methanol=30:1) to give 0.34 g of N-(2-ethoxycarbonylamino-5-fluorophenyl)-N-ethoxycarbonyl-N',N'-dimethylethylenediamine.

Mass spectrum (m/z): 342 (MH⁺).

NMR (CDCl₃) δ: 1.01–1.40 (6H, m), 2.27 (6H, s), 2.10–2.57 (2H, m), 2.90–3.30 (1H, m), 3.90–4.60 (5H, m), 6.74–7.12 (2H, m), 7.85–8.05 (1H, m), 10.59 (1H, br s)

(4) The following compound was prepared in generally the same manner as Example 1(4).

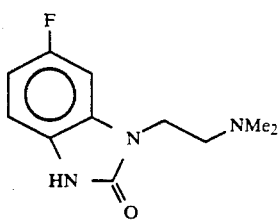

1,3-Dihydro-1-(2-dimethylaminoethyl)-6-fluoro-2H-benzimidazol-2-one.

Starting compound: N-(2-Ethoxycarbonylamino-5-fluorophenyl)-N-ethoxycarbonyl-N',N'-dimethylethylenediamine.

Mass spectrum (m/z) 224 (MH+).

NMR (CDCl$_3$) δ: 2.36 (6H, s), 2.66 (2H, t, J=7 Hz), 3.98 (2H, t, J=7 Hz), 6.72–6.84 (2H, m), 6.92–6.98 (1H, m), 9.42 (1H, br s).

(5) The following compound was prepared in generally the same manner as Example 2(4).

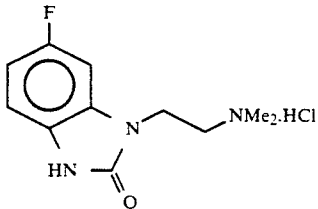

1,3-Dihydro-1-(2-dimethylaminoethyl)-6-fluoro-2H-benzimidazol-2-one hydrochloride.

Starting compound: 1,3-Dihydro-1-(2-dimethylaminoethyl)-6-fluoro-2H-benzimidazol-2-one.

mp: 232°–240° C.

| Analysis (for C$_{11}$H$_{15}$N$_3$OFCl.0.25H$_2$O) | | | | |
|---|---|---|---|---|
| C (%) | H (%) | N (%) | F (%) | Cl (%) |
| Calcd.: 50.01 | 5.91 | 15.90 | 7.19 | 13.42 |
| Found: 50.04 | 5.82 | 15.85 | 6.91 | 13.23 |

EXAMPLE 11

(1) The following compound was prepared in generally the same manner as Example 9(2).

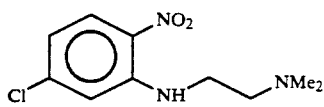

N-(5-Chloro-2-nitrophenyl)-N',N'-dimethylethylenediamine.

Starting compound: 5-Chloro-2-nitroaniline.

Mass spectrum (m/z): 244 (MH+).

NMR (CDCl$_3$) δ: 2.30 (6H, s), 2.63 (2H, t, J=6 Hz), 3.22–3.40 (2H, m), 6.59 (1H, dd, J=2 and 9 Hz), 6.82 (1H, d, J=2 Hz), 8.11 (1H, d, J=9 Hz), 8.38 (1H, br s).

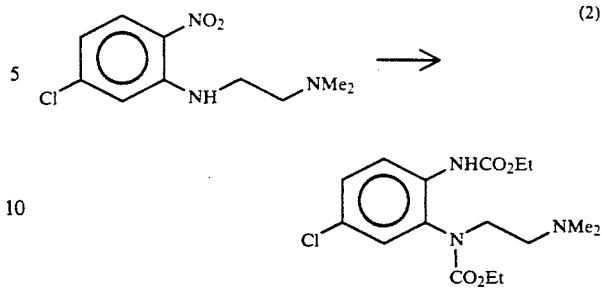

To a solution of N-(5-Chloro-2-nitrophenyl)-N',N'-dimethylethylenediamine (1.02 g) in ethyl acetate (10 ml) was added Raney nickel and the reaction mixture was stirred under a hydrogen atmosphere at atmospheric pressure at 5° C. for 1 hour. The reaction mixture was then filtered and the solvent was distilled off under reduced pressure. The residue was dissolved in dichloromethane (15 ml), followed by dropwise addition of triethylamine (1.28 g) and ethyl chloroformate (1.14 g) in turn at 5° C. with stirring. The reaction mixture was further stirred at room temperature for 1 hour and diluted with water (10 ml). The organic layer was washed with saturated aqueous sodium chloride solution and dried over anhydrous sodium sulfate. The solvent was distilled off under reduced pressure and the residue was purified by silica gel chromatography (eluent:chloroform:methanol=50:1) to give 1.05 g of N-(5-chloro-2-ethoxycarbonylaminophenyl)-N-ethoxycarbonyl-N',N'-dimethylethylenediamine.

Mass spectrum (m/z): 358 (MH+).

NMR (CDCl$_3$) δ: 1.00–1.40 (6H, m), 2.26 (6H, s), 2.12–2.70 (2H, m), 2.88–3.24 (1H, m), 3.80–4.60 (5H, m), 7.03 (1H, d, J=2 Hz), 7.22 (1H, dd, J=2 and 9 Hz), 7.94 (1H, d, J=9 Hz), 10.71 (1H, br s).

(3) The following compound was prepared in generally the same manner as Example 1(4).

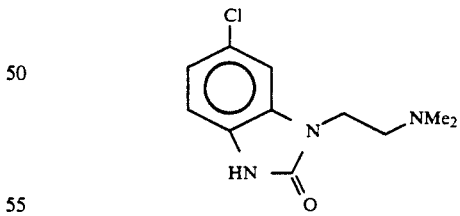

6-Chloro-1,3-dihydro-1-(2-dimethylaminoethyl)-2H-benzimidazol-2-one.

Starting compound: N-(5-Chloro-2-ethoxycarbonylaminoethyl)-N-ethoxycarbonyl-N', N'-dimethylethylenediamine.

Mass spectrum (m/z): 240 (MH+).

NMR (CDCl$_3$) δ: 2.34 (6H, s), 2.66 (2H, t, J=7 Hz), 3.96 (2H, t, J=7 Hz), 6.92–7.04 (3H, m), 10.31 (1H, br s).

(4) The following compound was prepared in generally the same manner as Example 2(4).

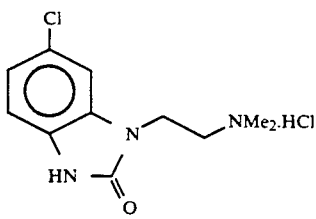

6-Chloro-1,3-dihydro-1-(2-dimethylaminoethyl)-2H-benzimidazol-2-one hydrochloride.

Starting compound: 6-Chloro-1,3-dihydro-1-(2-dimethylaminoethyl)-2H-benzimidazol-2-one.

mp: 257°–260° C.

|  | Analysis (for $C_{11}H_{15}N_3OCl_2$) | | | |
| --- | --- | --- | --- | --- |
|  | C (%) | H (%) | N (%) | Cl (%) |
| Calcd.: | 47.84 | 5.47 | 15.22 | 25.68 |
| Found: | 47.58 | 5.49 | 15.11 | 25.52 |

EXAMPLE 12

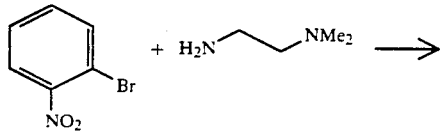 (1)

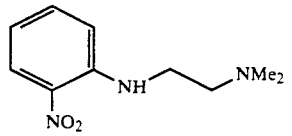

To a solution of 2-bromonitrobenzene (10.23 g) in 1-propanol (100 ml) was added N,N-dimethylethylenediamine (13.41 g) and the mixture was refluxed for 3 days. The solvent was then distilled off under reduced pressure and the residue was purified by silica gel chromatography (eluent: chloroform:methanol=50:1) to give 9.72 g of N-(2-nitrophenyl)-N',N'-dimethylethylenediamine.

Mass spectrum (m/z): 210 (MH+)

NMR (CDCl₃) δ: 2.31 (6H, s), 2.50–2.75 (2H, m), 3.25–3.45 (2H, m), 6.53–6.88 (2H, m), 7.33–7.53 (1H, m), 8.71 (1H, dd, J=1.5 and 8.5 Hz), 8.30 (1H, br s).

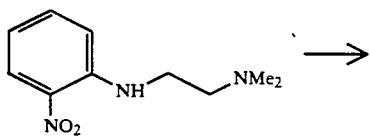 (2)

To a solution of N-(2-nitrophenyl)-N',N'-dimethylethylenediamine (9.70 g) in methanol (50 ml) were added concentrated hydrochloric acid (8 ml) and 10% palladium-on-carbon (0.97 g) and the mixture was stirred under a hydrogen atmosphere at atmospheric pressure for 3.5 hours. The catalyst was filtered off and the filtrate was distilled off under reduced pressure to give 11.70 g of N-(2-aminophenyl)-N',N'-dimethylethylenediamine dihydrochloride.

Mass spectrum (m/z): 180 (MH+-2 HCl).

NMR (DMSO-d₆) δ: 2.80 (6H, s), 3.10–3.70 (4H, m), 6.65–7.40 (4H, m), 9.30–11.00 (3H, m).

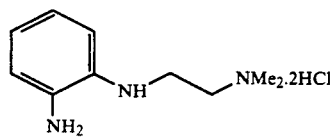 (3)

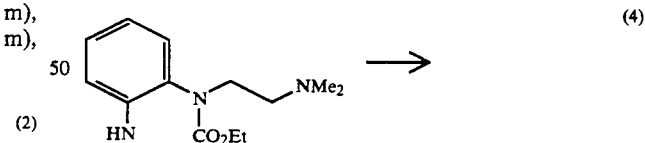

In 1N hydroxide solution (120 ml) was dissolved N-(2-aminophenyl)-N',N'-dimethylethylenediamine dihydrochloride (11.70 g) and the free amine was extracted with 100 ml of chloroform. The organic layer was dried over anhydrous sodium sulfate and concentrated to half the initial volume. To the solution was added ethyl chloroformate (10.13 g) dropwise, followed by addition of triethylamine (4.50 g). The reaction mixture was stirred at room temperature for 1 hour, after which it was successively washed with 1N aqueous sodium hydroxide solution and saturated sodium chloride solution and dried over anhydrous sodium sulfate. The solvent was then distilled off under reduced pressure and the residue was purified by silica gel chromatography (eluent: chloroform:methanol=50:1) to give 14.59 g of N-(2-ethoxycarbonylaminophenyl)-N-ethoxycarbonyl-N',N'-dimethylethylenediamine.

Mass spectrum (m/z): 324 (MH+).

NMR (CDCl₃) δ: 0.90–1.45 (6H, m), 2.00–3.25 (2H, m), 2.27 (6H, s), 3.75–4.70 (6H, m), 6.90–7.45 (3H, m), 7.90–8.05 (1H, m), 10.60 (1H, br s).

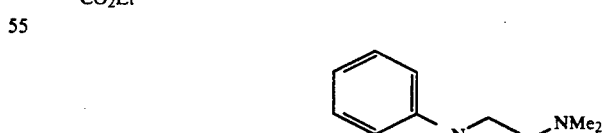 (4)

In ethanol (100 ml) was dissolved sodium metal (0.70 g) followed by addition of a solution of N-(2-ethoxycarbonylaminophenyl)-N-ethoxycarbonyl-N',N'-dimethylethylenediamine (4.88 g) in ethanol (20 ml). The mixture was refluxed overnight and the solvent was then distilled off under reduced pressure. To the residue was added chloroform and the insoluble matter was filtered off. The solvent was distilled off and the residue was purified by silica gel chromatography (eluent: chloroform:methanol=10:1) to give 2.69 g of 1,3-dihydro-1-(2-dimethylaminoethyl)-2H-benzimidazol-2-one.

Mass spectrum (m/z): 205 (M+).

NMR (CDCl$_3$) δ: 6 2.32 (6H, s), 2.64 (2H, t, J=7 Hz), 4.00 (2H, t, J=7 Hz), 6.94–7.12 (4H, m), 9.96 (1H, br s).

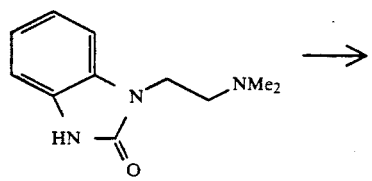

(5)

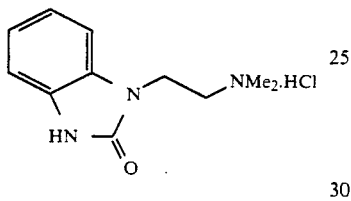

To a solution of 1,3-dihydro-1-(2-dimethylaminoethyl)-2H-benzimidazol-2-one (1.32 g) in ether (40 ml) was added 4N hydrogen chloride in dioxane dropwise with stirring. The separated crystals were collected by suction and dried to give 930 mg of 1,3-dihydro-1-(2-dimethylaminoethyl)-2H-benzimidazol-2-one hydrochloride.

mp: 206°–215° C.

| Analysis (for C$_{11}$H$_{16}$N$_3$OCl) | | | |
|---|---|---|---|
| | C (%) | H (%) | N (%) | Cl (%) |
| Calcd.: | 54.66 | 6.67 | 17.38 | 14.67 |
| Found: | 54.46 | 6.64 | 17.34 | 14.90 |

EXAMPLE 13

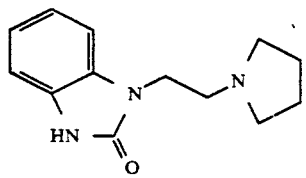

(1)

1,3-Dihydro-1-[2-(1-pyrrolidinyl)ethyl]-2H-benzimidazol-2-one was prepared in generally the same manner as Examples 12(3) and 12(4).

Mass spectrum (m/z): 232 (MH+).

NMR (CDCl$_3$) δ: 1.70–2.14 (4H, m), 2.50–3.00 (6H, m), 4.06 (2H, t, J=7 Hz), 6.85–7.15 (4H, m), 9.97 (1H, br s)

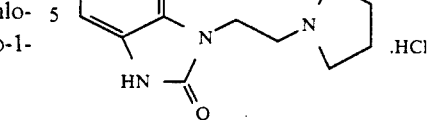

(2)

1,3-Dihydro-1-[2-(1-pyrrolidinyl)ethyl]-2H-benzimidazol-2-one hydrochloride was prepared in generally the same manner as Example 12(5).

mp: 188°–191° C.

| Analysis (for C$_{13}$H$_{18}$N$_3$OCl.0.7H$_2$O) | | | |
|---|---|---|---|
| | C (%) | H (%) | N (%) | Cl (%) |
| Calcd.: | 55.69 | 6.97 | 14.99 | 12.65 |
| Found: | 55.70 | 7.05 | 14.66 | 12.51 |

Mass spectrum (m/z): 232 (MH+-HCl).

EXAMPLE 14

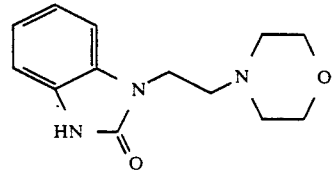

(1)

1,3-Dihydro-1-(2-morpholinoethyl)-2H-benzimidazol-2-one was prepared in generally the same manner as Examples 12(3) and 12(4).

Mass spectrum (m/z): 248 (MH+).

NMR (CDCl$_3$) δ: 2.44–2.80 (6H, m), 3.52–3.76 (4H, m), 4.00 (2H, t, J=7 Hz), 6.90–7.12 (4H, m), 10.03 (1H, br s).

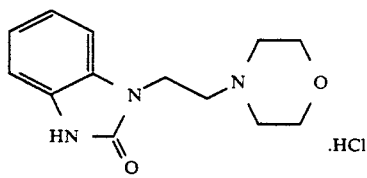

(2)

1,3-Dihydro-1-(2-morpholinoethyl)-2H-benzimidazol-2-one hydrochloride was prepared in generally the same manner as Example 12(5).

mp: 208°–220° C. (decompn.).

| Analysis (for C$_{13}$H$_{18}$N$_3$O$_2$Cl.0.2H$_2$O) | | | |
|---|---|---|---|
| | C (%) | H (%) | N (%) | Cl (%) |
| Calcd.: | 54.34 | 6.45 | 14.62 | 12.34 |
| Found: | 54.22 | 6.57 | 14.24 | 12.44 |

EXAMPLE 15

(1) The following compound was prepared in generally the same manner as Example 9(2).

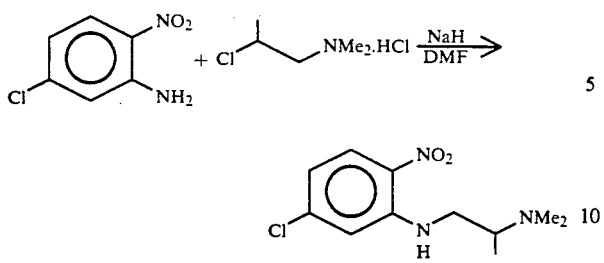

1-(5-Chloro-2-nitrophenyl)amino-2-dimethylaminopropane.

Starting compounds: 5-Chloro-2-nitroaniline and 2-dimethylaminoisopropyl chloride hydrochloride.

Mass spectrum (m/z): 257 (M+).

NMR (CDCl$_3$) δ: 1.10 (3H, d, J=5 Hz), 2.25 (6H, s), 2.80-3.30 (3H, m), 6.68 (1H, dd, J=2 and 12 Hz), 6.78 (1H, d, J=2 Hz), 8.10 (1H, d, J=12 Hz), 8.56 (1H, br s).

(2) The following compound was prepared in generally the same manner as Example 11(2).

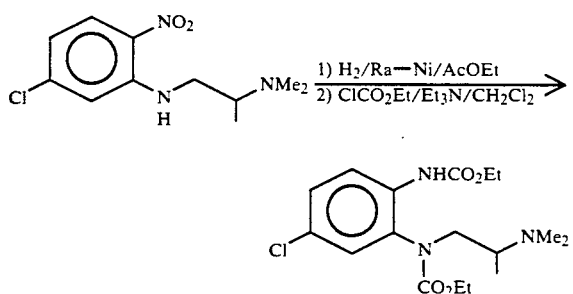

1-[N-(5-Chloro-2-ethoxycarbonylaminophenyl)-N-ethoxycarbonyl]amino-2-dimethylaminopropane.

Mass spectrum (m/z): 372 (MH+).

NMR (CDCl$_3$) δ: 0.75-0.95 (3H, m), 1.00-1.40 (6H, m), 2.10-2.40 (6H, m), 2.40-3.35 (2H, m), 3.75-4.65 (5H, m), 7.00-7.40 (2H, m), 7.92 (1H, d, J=9 Hz), 10.70-11.00 (1H, m).

(3) The following compound was prepared in generally the same manner as Example 1(4).

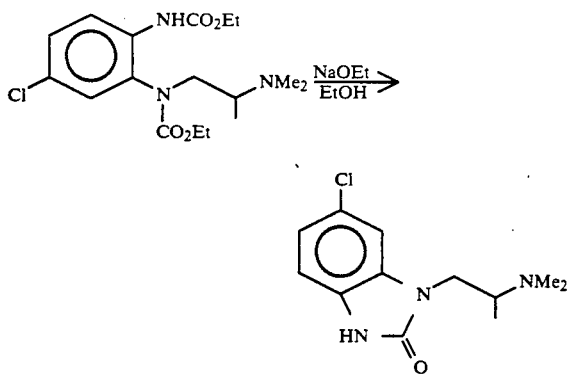

6-Chloro-1,3-dihydro-1-(2-dimethylaminopropyl)-2H-benzimidazol-2-one.

Mass spectrum (m/z): 254 (MH+).

NMR (CDCl$_3$) δ: 1.10 (3H, d, J=7 Hz), 2.36 (6H, s), 3.08-3.21 (1H, m), 3.85 (2H, ABX, J=8, 16 and 16 Hz), 6.88-7.10 (3H, m), 9.80 (1H, s).

(4) The following compound was prepared in generally the same manner as Example 2(4).

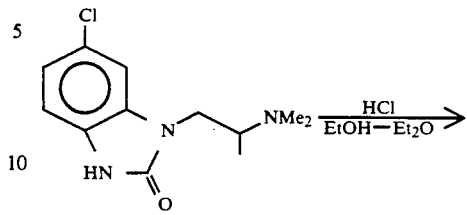

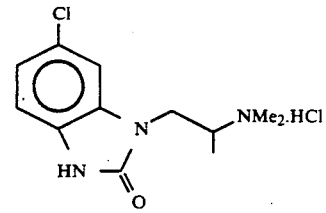

6-Chloro-1,3-dihydro-1-(2-dimethylaminopropyl)-2H-benzimidazol-2-one hydrochloride.

mp: 237°-244° C.

|  | Analysis (for C$_{12}$H$_{17}$N$_3$OCl$_2$) | | | |
| --- | --- | --- | --- | --- |
|  | C (%) | H (%) | N (%) | Cl (%) |
| Calcd.: | 49.67 | 5.90 | 14.48 | 24.43 |
| Found: | 49.45 | 5.90 | 14.43 | 24.46 |

EXAMPLE 16

(1) The following compound was prepared in generally the same manner as Example 8(1).

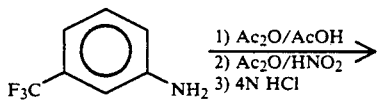

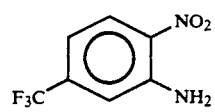

2-Nitro-5-trifluoromethylaniline.

Starting compound: 3-Trifluoromethylaniline.

Mass spectrum (m/z): 206 (M+).

NMR (CDCl$_3$) δ: 6.21 (1H, br s), 6.92 (1H, dd, J=2 and 12 Hz), 7.09 (1H, br s), 7.50-7.80 (1H, m), 8.24 (1H, d, J=12 Hz).

(2) The following compound was prepared in generally the same manner as Example 5(1).

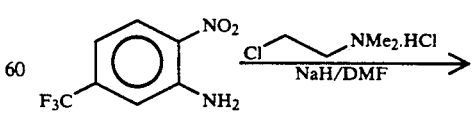

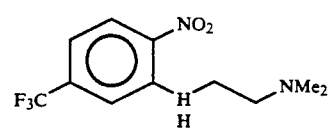

N,N-Dimethyl-N,-(2-nitro-5-trifluoromethylphenyl-)ethylenediamine.

Mass spectrum (m/z): 278 (MH+).

NMR (CDCl₃) δ: 2.32 (6H, s), 2.65 (2H, t, J=6 Hz), 3.27-3.46 (2H, m), 6.78-7.09 (2H, m), 8.22-8.50 (2H, m).

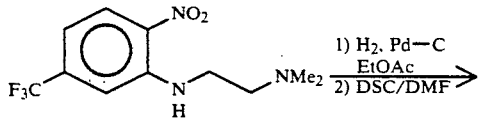

(3)

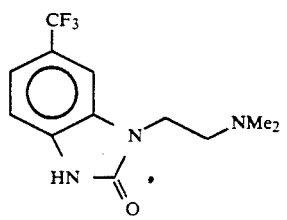

In ethyl acetate (20 ml) was dissolved N,N-dimethyl-N'-(2-nitro-5-trifluoromethylphenyl)ethylenediamine (0.24 g) followed by addition of a catalytic amount of 10% palladium-on-carbon, and the mixture was stirred under a hydrogen atmosphere at atmospheric pressure and room temperature until the absorption of hydrogen was ceased (for about 1 hour). The insoluble matter was filtered off and the solvent was distilled off under reduced pressure. The residue was dissolved in N,N-dimethylformamide (2 ml) followed by addition of N,N'-disuccinimidyl carbonate (DSC) (0.23 g). The reaction mixture was stirred at room temperature overnight, after which it was diluted with 1N hydrochloric acid and washed with ethyl acetate. The aqueous layer was alkalized with sodium hydroxide and the product was extracted with ethyl acetate. The organic layer was washed with saturated aqueous sodium chloride solution and dried over anhydrous sodium sulfate. The solvent was then distilled off under reduced pressure and the residue was purified by column chromatography (eluent:chloroform:methanol=5:1) to give 0.11 g of 1,3-dihydro-1-(2-dimethylaminoethyl)-6-trifluoromethyl-2H-benzimidazol-2-one.

Mass spectrum (m/z): 274 (MH+).

NMR (CDCl₃) δ: 6: 2.35 (6H, s), 2.69 (2H, t, J=9 Hz), 4.03 (2H, t, J=9 Hz), 6.97-7.34 (3H, m), 9.58 (1H, br s).

(4) The following compound was prepared in generally the same manner as Example 2(4).

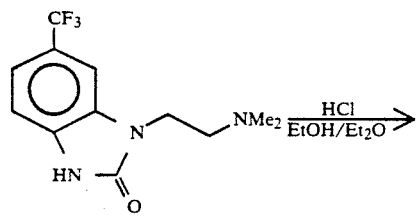

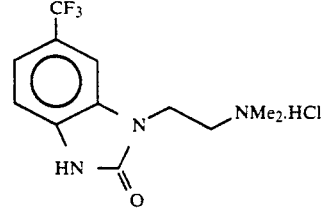

1,3-Dihydro-1-(2-dimethylaminoethyl)-6-trifluoromethyl-2H-benzimidazol-2-one hydrochloride.
mp: 229°-234 ° C.

| Analysis (for C₁₂H₁₅N₃OClF₃) | | | | | |
|---|---|---|---|---|---|
| | C (%) | H (%) | N (%) | Cl (%) | F (%) |
| Calcd.: | 46.54 | 4.88 | 13.57 | 11.45 | 18.40 |
| Found: | 46.39 | 4.91 | 13.27 | 11.46 | 18.11 |

EXAMPLE 17

(1) The following compound was prepared in generally the same manner as Example 5(1).

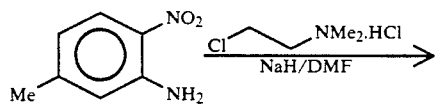

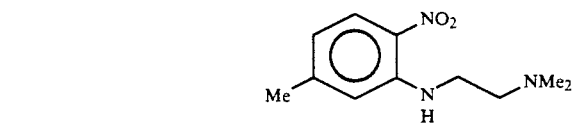

N,N-Dimethyl-N,-(5-methyl-2-nitrophenyl)ethylenediamine.

Starting compounds: 2-Nitro-5-methylaniline and 2-chloroethyldimethylamine hydrochloride.

Mass spectrum (m/z): 224 (MH+).

NMR (CDCl₃) δ: 2.30 (3H, s), 2.34 (3H, s), 2.50-2.69 (2H, m), 3.25-3.44 (2H, m), 6.44 (1H, dd, J=1.5 and 9 Hz), 6.60 (1H, d, J=1.5 Hz), 8.06 (1H, d, J=9 Hz), 8.33 (1H, br s).

(2) The following compound was prepared in generally the same manner as Example 5(2).

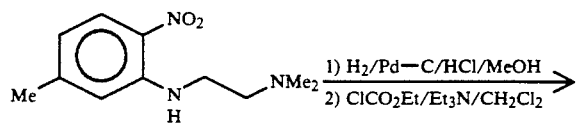

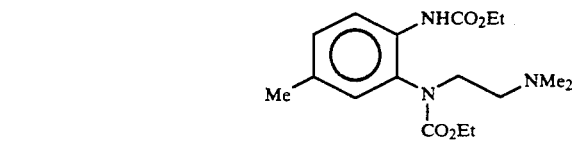

N-(2-Ethoxycarbonylamino-5-methylphenyl)-N-ethoxycarbonyl-N',N'-dimethylethylenediamine.

Mass spectrum: 338 (MH+).

NMR (CDCl₃) δ: 1.00-1.35 (6H, m), 2.26 (6H, s), 2.29-2.52 (2H, m), 2.90-3.16 (1H, m), 3.80-4.60 (5H, m), 6.88 (1H, d, J=1 Hz), 7.08 (1H, dd, J=1 and 8 Hz), 7.82 (1H, d, J=8 Hz), 10.45 (1H, br s).

(3) The following compound was prepared in generally the same manner as Example 1(4).

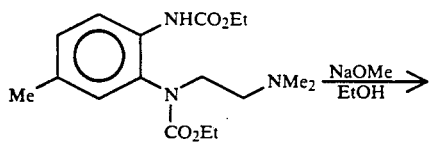

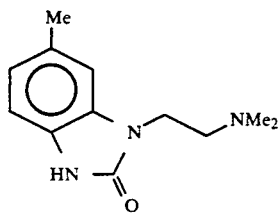

1,3-Dihydro-1-(2-dimethylaminoethyl)-6-methyl-2H-benzimidazol-2-one.

Mass spectrum: 220 (MH+).

NMR (CDCl3) δ: 2.34 (6H, s), 2.38 (3H, s), 2.64 (2H, t, J=7 Hz), 3.97 (2H, t, J=7 Hz), 6.80–7.00 (3H, m), 9.56 (1H, br s), (4) The following compound was prepared in generally the same manner as Example 2(4).

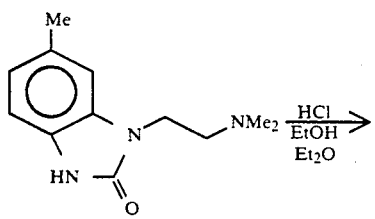

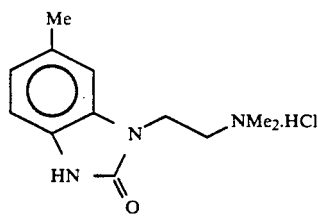

1,3-Dihydro-1-(2-dimethylaminoethyl)-6-methyl-2H-benzimidazol-2-one hydrochloride.

mp: 238°–241° C.

| Analysis (for C12H18N3OCl) | | | |
|---|---|---|---|
| C (%) | H (%) | N (%) | Cl (%) |
| Calcd.: 56.36 | 7.09 | 16.43 | 13.86 |
| Found: 56.23 | 7.04 | 16.33 | 13.75 |

EXAMPLE 18

(1) The following compound was prepared in generally the same manner as Example 1(1).

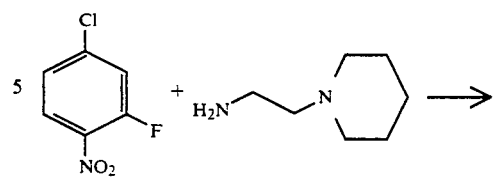

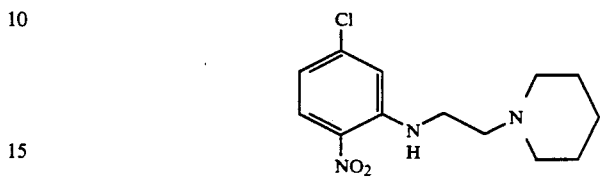

1-[2-(5-Chloro-2-nitrophenylamino)ethyl]piperidine.

Starting compounds: 4-Chloro-2-fluoronitrobenzene and 1-(2-aminoethyl)piperidine.

mp: 105°–106° C.

Mass Spectrum: 283, 285 (M+).

NMR (CDCl3) δ: 1.30–1.70 (6H, m), 2.35–2.6 (4H, m), 2.65 (2H, t, J=6 Hz), 3.31 (2H, q, J=6 Hz), 6.57 (1H, dd, J=2, 9 Hz), 6.82 (1H, d, J=2 Hz), 8.11 (1H, d, J=9 Hz), 8.6 (1H, br).

(2)

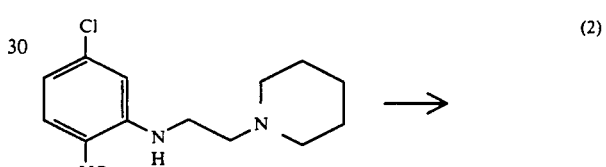

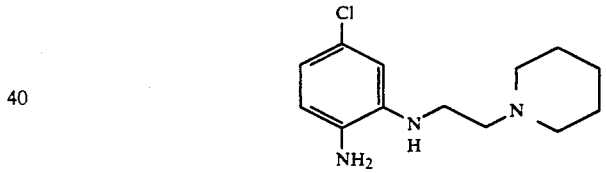

In ethyl acetate (120 ml) was dissolved 1-[2-(2-amino-5-chlorophenylamino)ethyl]piperidine (2.73 g) followed by addition of Raney nickel (0.5 g), washed in advance with ethyl acetate, and ethanol (0.5 ml). The mixture was stirred under a hydrogen atmosphere at atmospheric pressure until 650 ml of hydrogen had been taken up. The insoluble matter was then filtered off and the solvent was distilled off under reduced pressure to give 2.43 g of 1-[2-(2-amino-5-chlorophenylamino)ethyl]piperidine as a semisolid.

Mass spectrum (m/z) 253, 255 (M+).

NMR (CDCl3) δ: 1.30–1.70 (6H, m), 2.30–2.50 (4H, m), 2.59 (2H, t, J=6 Hz), 3.10 (2H, q, J=6 Hz), 3.34 (2H, br s), 4.14 (1H, br s), 6.58 (3H, br s).

(3)

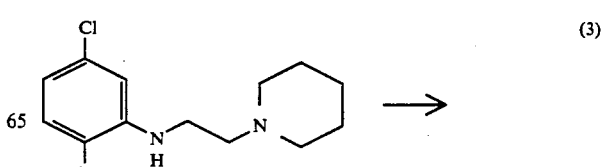

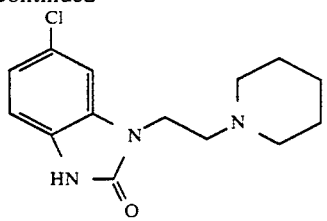

To a solution of 1-[2-(2-amino-5-chlorophenylamino)ethyl]piperidine (2.41 g) in N,N-dimethylformamide (20 ml) was added N,N'-disuccinimidyl carbonate (2.68 g) over a period of 15 minutes. The mixture was stirred at room temperature overnight and diluted with 5% hydrochloric acid (150 ml). The aqueous solution was washed with ethyl acetate, alkalized with 10% aqueous sodium hydroxide solution and extracted with ethyl acetate. The organic layer was successively washed with water ($\times$3) and saturated sodium chloride solution and dried over anhydrous sodium sulfate. The solvent was distilled off under reduced pressure to give a crude crystalline product (2.50 g). Recrystallization from ethyl acetate (28 ml) gave 2.12 g of 6-chloro-1,3-dihydro-1(2-piperidinoethyl)-2H-benzimidazol-2-one as colorless crystals.

mp: 156°–158.5° C.

| Analysis (for $C_{14}H_{18}N_3OCl$) | | | |
|---|---|---|---|
| C (%) | H (%) | N (%) | Cl (%) |
| Calcd.: 60.10 | 6.48 | 15.02 | 12.67 |
| Found: 59.98 | 6.43 | 15.00 | 12.72 |

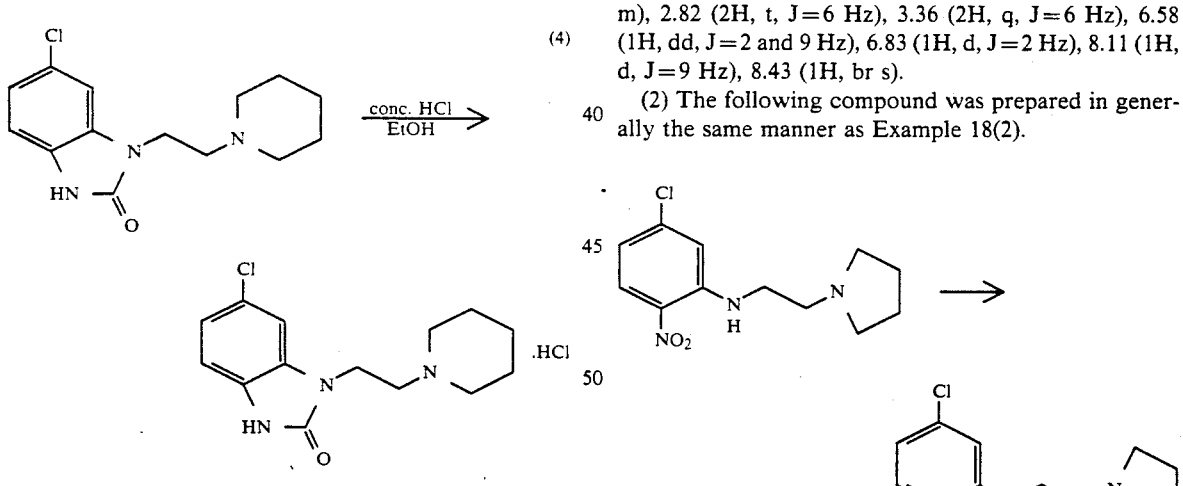

(4)

To a solution of 6-chloro-1,3-dihydro-1-(2-piperidinoethyl)-2H-benzimidazol-2-one in ethanol (30 ml) was added concentrated hydrochloric acid (330 μl) and the mixture was allowed to stand for 4 hours. The separating crystals were collected by suction and dried at 60° C. under reduced pressure to give 1.05 g of 6-chloro-1,3-dihydro-1-(2-piperidinoethyl)-2H-benzimidazol-2-one hydrochloride.

mp: 278°–282° C.

| Analysis (for $C_{14}H_{19}N_3OCl_2$) | | | |
|---|---|---|---|
| C (%) | H (%) | N (%) | Cl (%) |
| Calcd.: 53.17 | 6.06 | 13.29 | 22.42 |
| Found: 52.92 | 6.23 | 13.19 | 22.23 |

EXAMPLE 19

(1) The following compound was prepared in generally the same manner as Example 18(1).

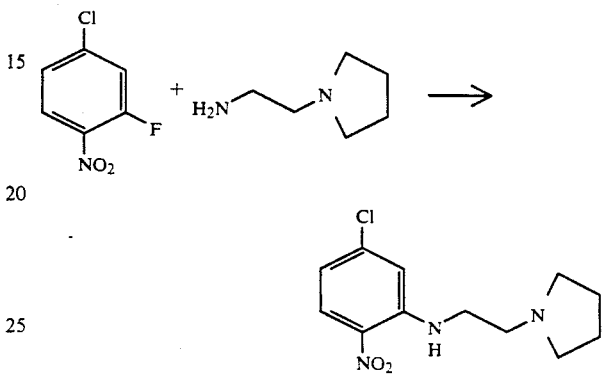

1-[2-(5-Chloro-2-nitrophenylamino)ethyl]pyrrolidine.

Starting compounds: 4-Chloro-2-fluoronitrobenzene and 1-(2-aminoethyl)pyrrolidine.

mp: 77°–77.5° C.

Mass spectrum (m/z): 269, 271 (M+).

NMR (CDCl$_3$) δ: 1.70–1.90 (4H, m), 2.45–2.70 (4H, m), 2.82 (2H, t, J=6 Hz), 3.36 (2H, q, J=6 Hz), 6.58 (1H, dd, J=2 and 9 Hz), 6.83 (1H, d, J=2 Hz), 8.11 (1H, d, J=9 Hz), 8.43 (1H, br s).

(2) The following compound was prepared in generally the same manner as Example 18(2).

1-[2-(2-Amino-5-chlorophenylamino)ethyl]pyrrolidine.

Starting compound: 1-[2-(5-Chloro-2-nitrophenylamino)ethyl]pyrrolidine.

Mass spectrum (m/z): 239, 241 (M+).

NMR (CDCl$_3$) δ: 1.60–2.00 (4H, m), 2.40–2.60 (4H, m), 2.60–2.80 (2H, m), 3.05–3.25 (2H, m), 3.35 (2H, br s), 4.05 (1H, br), 6.60 (3H, br s).

(3) The following compound was prepared in generally the same manner as Example 18(3).

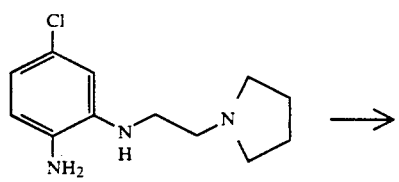

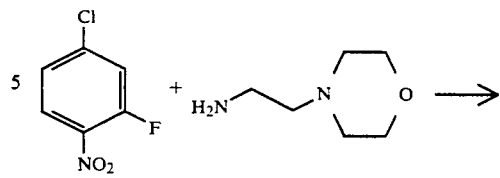

6-Chloro-1,3-dihydro-1-[2-(1-pyrrolidinyl)ethyl]-2H-benzimidazol-2-one.

Starting compound: 1-[2-(2-Amino-5-chlorophenylamino)ethyl]pyrrolidine.

mp: 146°–148° C.

| | Analysis (for C₁₃H₁₆N₃OCl) | | | |
|---|---|---|---|---|
| | C (%) | H (%) | N (%) | Cl (%) |
| Calcd.: | 58.76 | 6.07 | 15.81 | 13.34 |
| Found: | 58.87 | 6.09 | 15.90 | 13.44 |

(4) The following compound was prepared in generally the same manner as Example 18(4).

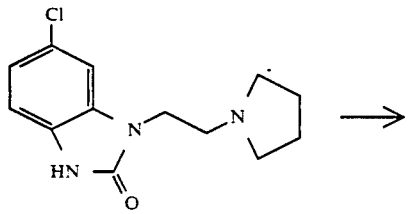

6-Chloro-1,3-dihydro-1-[2-(1-pyrrolidinyl)ethyl]-2H-benzimidazol-2-one hydrochloride.

Starting compound: 6-Chloro-1,3-dihydro-1-[2-(1pyrrolidinyl)ethyl]-2H-benzimidazol-2-one.

mp: 261°–265° C.

| | Analysis (for C₁₃H₁₇N₃OCl₂) | | | |
|---|---|---|---|---|
| | C (%) | H (%) | N (%) | Cl (%) |
| Calcd.: | 51.67 | 5.67 | 13.90 | 23.46 |
| Found: | 51.62 | 5.66 | 13.92 | 23.42 |

EXAMPLE 20

(1) The following compound was prepared in generally the same manner as Example 1(1).

1-[2-(5-Chloro-2-nitrophenylamino)ethyl]morpholine.

Starting compounds: 4-Chloro-2-fluoronitrobenzene and 1-(2-aminoethyl)morpholine.

mp: 125.5°–126° C.

Mass spectrum (m/z): 285, 287 (M+).

NMR (CDCl₃) δ: 2.45–2.55 (4H, m), 2.75–2.90 (2H, m), 3.24–3.40 (2H, m), 3.70–3.80 (4H, m), 6.59 (1H, dd, J=2, 9 Hz), 6.81 (1H, d, J=2 Hz), 8.12 (1H, d, J=9 Hz), 8.56 (1H, br s).

(2) The following compound was prepared in generally the same manner as Example 18(2).

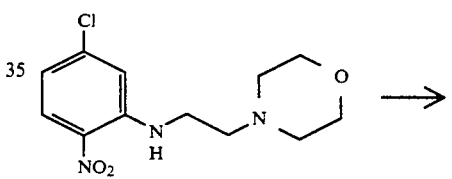

1--[2-(2-Amino-5-chlorophenylamino)ethyl]morpholine.

Starting compound: 1-[2-(5-Chloro-2-nitrophenylamino)ethyl]morpholine.

Mass spectrum (m/z) 255, 257 (M+).

NMR (CDCl₃) δ: 2.40–2.55 (4H, m), 2.55–2.70 (2H, m), 3.05–3.20 (2H, m), 3.25 (2H, br s), 3.60–3.80 (4H, m), 4.10 (1H, br s), 6.59 (3H, br s).

(3) The following compound was prepared in generally the same manner as Example 18(3).

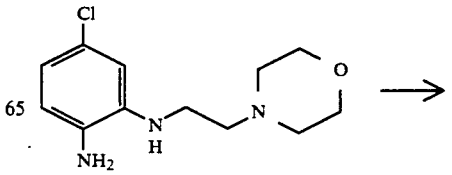

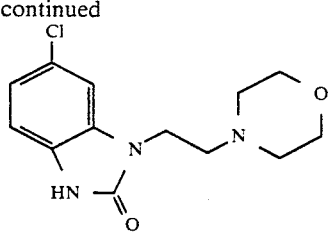

6-Chloro-1,3-dihydro-1-(2-morpholinoethyl)-2H-benzimidazol-2-one.

Starting compound: 1-[2-(2-Amino-5-chlorophenylamino)ethyl]morpholine.

mp: 159°-161° C.

| Analysis (for $C_{13}H_{16}N_3O_2Cl$) | | | |
|---|---|---|---|
| | C (%) | H (%) | N (%) | Cl (%) |
| Calcd.: | 55.42 | 5.72 | 14.91 | 12.59 |
| Found: | 55.34 | 5.63 | 14.86 | 12.71 |

(4) The following compound was prepared in generally the same manner as Example 18(4).

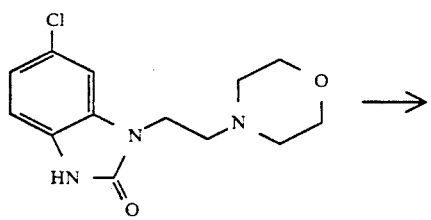

6-Chloro-1,3-dihydro-1-(2-morpholinoethyl)-2H-benzimidazol-2-one hydrochloride.

Starting compound: 6-Chloro-1,3-dihydro-1-(2-morpholinoethyl)-2H-benzimidazol-2-one.

mp: 252°-256° C.

| Analysis (for $C_{13}H_{17}N_3O_2Cl_2$) | | | |
|---|---|---|---|
| | C (%) | H (%) | N (%) | Cl (%) |
| Calcd.: | 49.07 | 5.38 | 13.21 | 22.28 |
| Found: | 49.18 | 5.39 | 13.13 | 22.24 |

EXAMPLE 21

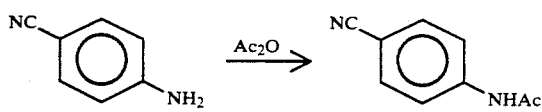

To 4-aminobenzonitrile (7.26 g) was added acetic anhydride (20 ml) and the mixture was stirred at room temperature for 30 minutes. The reaction mixture was diluted with water and the separated crystals were collected by suction, washed with water and dried under reduced pressure to give 9.40 g of 4-acetamidobenzonitrile.

Mass spectrum (m/z): 160 (M+).

NMR (CDCl$_3$) δ: 1.89 (2H, br s), 2.22 (3H, s), 7.40-7.70 (4H, m).

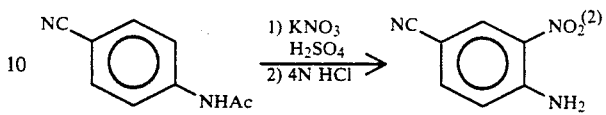

To a solution of 4-acetamidobenzonitrile (9.40 g) in concentrated sulfuric acid (80 ml) was added potassium nitrate in small portions at a temperature not exceeding 10° C. The reaction mixture was stirred at 5°-10° C. for 2 hours and poured into ice-water and the separated crystals were collected by suction. To the crystals was added 4N hydrochloric acid (100 ml) and the mixture was refluxed for 2 hours. After cooling to room temperature, the crystals were recovered by filtration, washed with water and dried under reduced pressure to give 7.22 g of 4-amino-3-nitrobenzonitrile.

Mass spectrum (m/z): 163 (M+).

NMR (DMSO-d$_6$) δ: 7.00-7.14 (1H, m), 7.60-8.10 (3H, m), 8.40-8.60 (1H, m).

(3) The following compound was prepared in generally the same manner as Example 9(2).

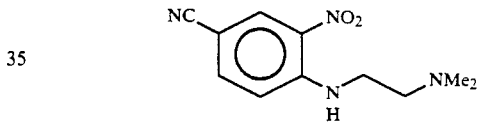

N-(4-Cyano-2-nitrophenyl)-N',N'-dimethylethylenediamine.

Staring compound: 4-Amino-3-nitrobenzonitrile.

Mass spectrum (m/z): 235 (MH+).

NMR (CDCl$_3$) δ: 2.31 (6H, s), 2.65 (2H, t, J=6 Hz), 3.28-3.46 (2H, m), 6.87 (1H, d, J=9 Hz), 7.60 (1H, dd, J=1, 9 Hz), 8.51 (1H, d, J=1 Hz), 8.78 (1H, br s).

(4) The following compound was prepared in generally the same manner as Example 16(3).

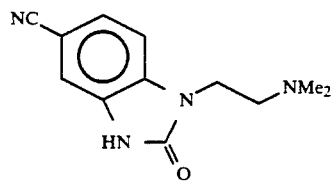

5-Cyano-1,3-dihydro-1-(2-dimethylaminoethyl)-2H-benzimidazol-2-one.

Starting compound: N-(4-Cyano-2-nitrophenyl)-N',N'-dimethylethylenediamine.

Mass spectrum (m/z): 231 (MH+).

NMR (CDCl$_3$) δ: 2.37 (6H, s), 2.72 (2H, d, J=7 Hz), 4.04 (2H, t, J=7 Hz), 7.01-7.45 (3H, m), 10.65 (1H, br s).

(5) The following compound was prepared in generally the same manner as Example 1(6).

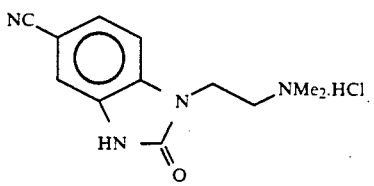

5-Cyano-1,3-dihydro-1-(2-dimethylaminoethyl)-2H-benzimidazol-2-one hydrochloride.

Starting compound: 5-Cyano-1,3-dihydro-1-(2-dimethylaminoethyl)-2H-benzimidazol-2-one.

mp: 246°–249° C.

| Analysis (for $C_{12}H_{15}N_4OCl \cdot 1.8H_2O$) | | | |
|---|---|---|---|
| | C (%) | N (%) | Cl (%) |
| Calcd.: | 48.18 | 18.73 | 11.85 |
| Found: | 48.03 | 18.61 | 12.18 |

EXAMPLE 22

(1) The following compound was prepared in generally the same manner as Example 21(1).

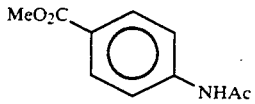

Methyl 4-acetamidobenzoate.
Starting compounds: Methyl 4-aminobenzoate.
Mass spectrum (m/z): 193 (M+).
NMR (CDCl$_3$) δ: 2.21 (3H, s), 3.90 (3H, s), 7.41 (1H, br s), 7.58 (2H, d, J=9 Hz), 8.01 (2H, d, J=9 Hz), (2) The following compound was prepared in generally the same manner as Example 21(2).

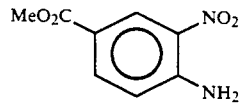

Methyl 4-amino-2-nitrobenzoate,
Starting compound: Methyl 4-acetamidobenzoate,
Mass spectrum (m/z): 196 (M+).
NMR (DMSO-d$_6$) δ: 3.82 (3H, s), 7.06 (1H, d, J=9 Hz), 7.80–7.93 (3H, m), 8 55 (1H, d, J=2 Hz), (3) The following compound was prepared in generally the same manner as Example 9(2).

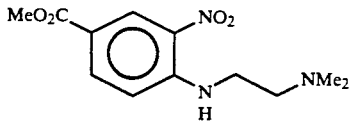

N,N-Dimethyl-N'-(4-methoxycarbonyl-2-nitrophenyl)ethylenediamine.
Starting compound: Methyl 4-amino-2-nitrobenzoate.
Mass spectrum (m/z): 268 (MH+).
NMR (CDCl$_3$) δ: 2.34 (6H, s), 2.67 (2H, t, J=6 Hz), 3.37–3.73 (2H, m), 3.91 (3H, s), 6.90 (1H, d, J=9 Hz), 8.06 (1H, dd, J=2 and 9 Hz), 8.69 (1H, br s), 8.88 (1H, d, J=2 Hz).

(4) The following compound was prepared in generally the same manner as Example 16(3).

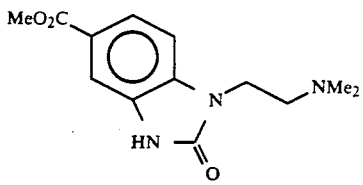

1,3-Dihydro-1-(2-dimethylaminoethyl)-5-methoxycarbonyl-2H-benzimidazol-2-one.
Starting compound: N,N-Dimethyl-N'-(4-methoxycarbonyl-2nitrophenyl)ethylenediamine.
Mass spectrum (m/z): 264 (MH+).
NMR (CDCl$_3$) δ: 2.37 (6H, s), 2.73 (2H, t, J=7 Hz), 3.90 (3H, s), 4.04 (2H, t, J=7 Hz), 7.00 (1H, d, J=8 Hz), 7.55 (1H, d, J=1 Hz), 7.80 (1H, dd, J=1 and 8 Hz), 10.10 (1H, br s).

(5) The following compound was prepared in generally the same manner as Example 1(6).

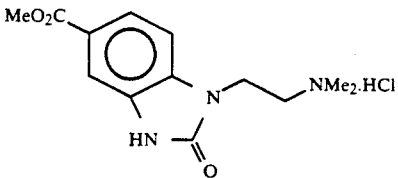

1,3-Dihydro-1-(2-dimethylaminoethyl)-5-methoxycarbonyl-2H-benzimidazol-2-one hydrochloride.
Starting compound: 1,3-Dihydro-1-(2-dimethylaminoethyl)-5-methoxycarbonyl-2H-benzimidazol-2-one.
mp: 229°–231° C.

| Analysis (for $C_{13}H_{18}N_3O_3Cl$) | | | |
|---|---|---|---|
| | C (%) | H (%) | N (%) | Cl (%) |
| Calcd.: | 52.09 | 6.05 | 14.02 | 11.53 |
| Found: | 51.93 | 6.01 | 13.97 | 11.92 |

EXAMPLE 23

(1)

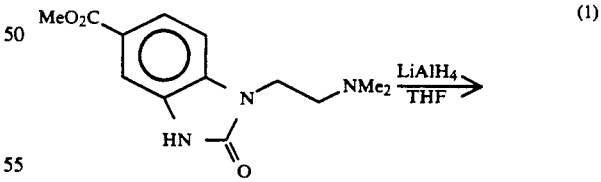

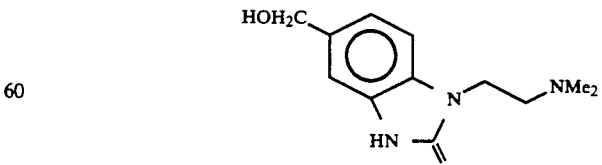

To a solution of 0.37 g of 1,3-dihydro-1-(2dimethylaminoethyl)-5-methoxycarbonyl-2H-benzimidazol-2-one in 15 ml of tetrahydrofuran was added 0.10 g of lithium aluminum hydride. After being stirred for 1 hour at room temperature, the reaction was quenched by the addition of 3.0 g of sodium sulfate hydrate. The solid was removed by filtration and the solvent was evaporated in vacuo. The residue was chromatographed on silica gel using chloroform-methanol-ammonium hydroxide (40:10:1) to provide 0.20 g of 1,3-dihydro-1-(2-dimethylaminoethyl)-5-hydroxymethyl-2H-benzimidazol-2-one.

Mass spectrum (m/z): 235 (M+).

NMR (DMSO-d6) δ: 2.23 (6H, s), 2.55 (2H, t, J=7 Hz), 3.87 (2H, t, J=7 Hz), 4.51 (2H, d, J=6 Hz), 4.95 (1H, t, J=6 Hz), 6.90-7.10 (3H, m), 10.65 (1H, s).

(2) The following compound was prepared in generally the same manner as example 1(6).

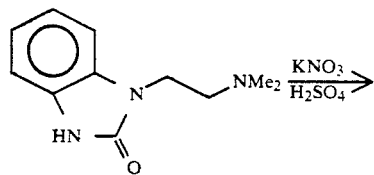

1,3-Dihydro-1-(2-dimethylaminoethyl)-5-hydroxymethyl-2H-benzimidazol-2-one hydrochloride.

Starting compound: 1,3-Dihydro-1-(2-dimethylaminoethyl)-5-hydroxymethyl-2H-benzimidazol-2-one.

mp: 222°–225° C.

| | Analysis (for $C_{12}H_{18}N_3O_2Cl.0.15H_2O$) | | | |
|---|---|---|---|---|
| | C (%) | H (%) | N (%) | Cl (%) |
| Calcd.: | 52.52 | 6.72 | 15.31 | 12.92 |
| Found: | 52.58 | 6.56 | 15.23 | 13.03 |

EXAMPLE 24

(1)
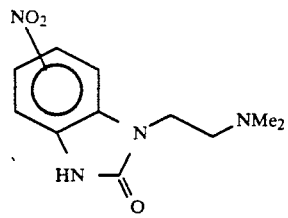

To a solution of 2.03 g of 1,3-dihydro-1-(2-dimethylaminoethyl)-2H-benzimidazol-2-one in 15 ml of sulfuric acid cooled to 0° C. was added in small portions 1.10 g of potassium nitrate. The reaction mixture was stirred at 15° C. for 2 hours, poured into ice-water and neutralized with sodium bicarbonate. After being extracted with ethyl acetate, dried over anhydrous sodium sulfate, and concentrated in vacuo, the crude material was chromatographed on silica gel. Elution with chloroform-methanol-ammonium hydroxide (100:10:1) afforded 1.76 g of 1:1 mixture of 1,3-dihydro-1-(2-dimethylaminoethyl)-5-nitro-2H-benzimidazol-2one and 1,3-dihydro-1-(2-dimethylaminoethyl)-6-nitro-2H-benzimidazol-2-one.

Mass spectrum (m/z): 251 (MH+).

NMR (DMSO-d6) δ: 2.17, 2.18 (6H, s), 2.47-2.61 (2H, m) 3.89-4.06 (2H, m), 7.10-7.41 (1H, m), 7.75-8.07 (2H, m), 11.51 (1H, br s).

(2) The following compound was prepared in generally the same manner as example 1(6).

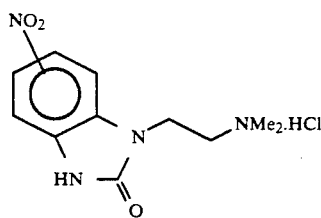

A 1:1 mixture of 1,3-dihydro-1-(2-dimethylaminoethyl)-5-nitro-2H-benzimidazol-2-one hydrochloride and 1,3-dihydro-1-(2-dimethylaminoethyl)-6-nitro-2H-benzimidazol-2-one hydrochloride.

Starting compound: A mixture of 1,3-dihydro-1-(2-dimethylaminoethyl)-5-nitro-2H-benzimidazol-2-one and 1,3-dihydro-1-(2-dimethylaminoethyl)-6-nitro-2H-benzimidazol-2one,

| | Analysis (for $C_{11}H_{15}N_4O_3Cl.0.7H_2O$) | | | |
|---|---|---|---|---|
| | C (%) | H (%) | N (%) | Cl (%) |
| Calcd.: | 44.14 | 5.52 | 18.72 | 11.84 |
| Found: | 44.19 | 5.12 | 18.65 | 12.09 |

The ratio of the mixture was confirmed as 1:1, since the ratio of NMR (CDCl3) integrations at 6 7.20 (d, J=8.6 Hz) assigned to 4-H of 6-nitrobenzimidazolone and 6 7.53 (d, J=8.8 Hz) assigned to 7-H of 5-nitrobenzimidazolone is exactly 1:1.

EXAMPLE 25

(1) The following compound was prepared in generally the same manner as Example 9(2).

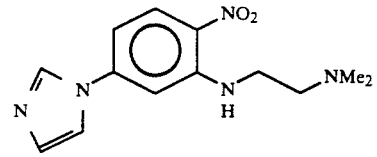

N,N-Dimethyl-N'-[5-(1-imidazolyl-2-nitrophenyl)ethylenediamine.

Starting compound: 5-(1-imidazolyl)-2-nitroaniline.

Mass spectrum (m/z): 275 (M+).

NMR (CDCl3) δ: 2 33 (6H, s). 2.66 (2H, t, J=6 Hz), 3.28-3.50 (2H, m), 6.61-6.80 (2H, m), 7.24-7.35 (2H, m), 7.94 (1H, s). 8.31 (1H, d, J=9 Hz), 8.55 (1H, br s), (2) The following compound was prepared in generally the same manner as Example 16(3).

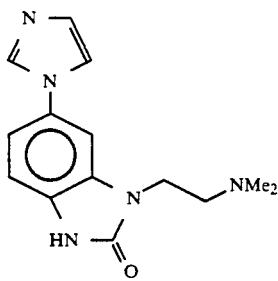

1.3-Dihydro-1-(2-dimethylaminoethyl)-6-(1-imidazolyl)-2H-benzimidazol-2-one.

Starting compound: N,N-Dimethyl-N,-[5-(1-imidazolyl-2-nitrophenyl)ethylenediamine.

Mass spectrum (m/z) 271 (M+).

NMR (CDCl₃) δ: 2.35 (6H, s), 2.69 (2H, t, J=7 Hz), 4.03 (2H, t, J=7 Hz), 7.08-7.26 (5H, m), 7.82 (1H, m), 10.06 (1H, br s).

(3) The following compound was prepared in generally the same manner as Example 2(4).

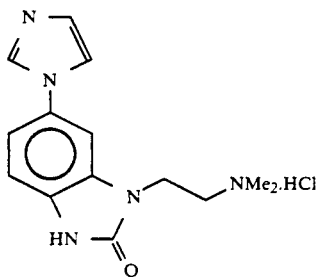

1,3-Dihydro-1-(2-dimethylaminoethyl)-6-(1-imidazolyl)-2H-benzimidazol-2-one hydrochloride.

Starting compound: 1,3-Dihydro-1-(2-dimethylaminoethyl)-6-(1-imidazolyl)-2H-benzimidazol-2-one.

mp: 220°-226° C.

| Analysis (for C₁₄H₁₉N₅OCl₂.H₂O) | | | |
|---|---|---|---|
| C (%) | H (%) | N (%) | Cl (%) |
| Calcd.: 46.42 | 5.84 | 19.33 | 19.57 |
| Found: 46.35 | 5.80 | 19.41 | 19.86 |

EXAMPLE 26

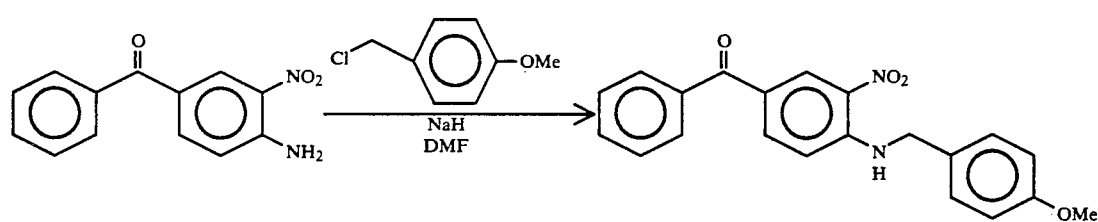

To a solution of 2.20 g of 4-amino-3-nitrobenzophenone and 1.57 g of 4-methoxybenzyl chloride in 25 ml of N,N-dimethylformamide was added at room temperature 0.40 g of 60% dispersion of sodium hydride in mineral oil, and the mixture was stirred overnight. After addition of saturated ammonium chloride aqueous solution was completed, the reaction mixture diluted with ethyl acetate was washed with brine. Removal of the solvent under reduced pressure gave the crude product, which was chromatographed on silica gel. Elution with hexane-ethyl acetate (3:1) provided 1.95 g of 4-(4-methoxybenzylamino)-3-nitrobenzophenone.

Mass spectrum (m/z): 362 (M+)

NMR (CDCl₃) δ: 3.81 (3H, s), 4.55 (2H, d, J=5.5 Hz), 6.91 (2H, d, J=8.7 Hz), 6.95 (1H, d, J=9.0 Hz), 7.28 (2H, d, J=8.7 Hz), 7.5-7.8 (5H, m), 8.00 (1H, ddd, J=9.0, 1.8 and 0.3 Hz), 8.69 (1H, d, J=2.0 Hz), 8.8 (1H, br s).

(2) The following compound was prepared in generally the same manner as Example 18(2).

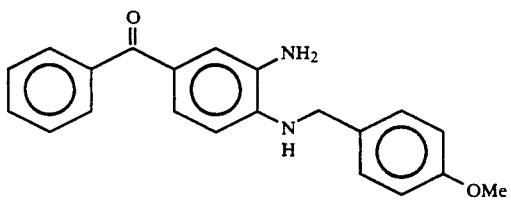

3-Amino-4-(4-methoxybenzylamino)benzophenone.

Starting compound: 4-(4-methoxybenzylamino)-3-nitrobenzophenone.

Mass spectrum (m/z): 332 (M+).

NMR (CDCl₃) δ: 3.3 (2H, br s), 3.78 (3H, s), 4.30 (2H, d, J=3.9 Hz), 4.5 (1H, br s), 6.58 (1H, d, J=8.3 Hz), 7.2-7.5 (5H, m), 7.70 (2H, d, J=7.3 Hz).

(3) The following compound was prepared in generally the same manner as Example 18(3).

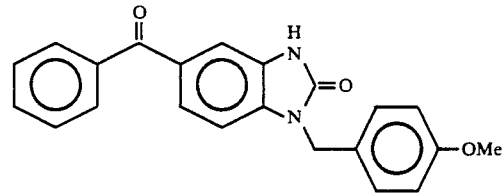

5-Benzoyl-1,3-dihydro-1-(4-methoxybenzyl)-2H-benzimidazol-2-one.

Starting compound: 3-Amino-4-(4-methoxybenzylamino)benzophenone.

Mass spectrum (m/z): 358 (M+).

NMR (CDCl₃) δ: 3.79 (3H, s), 5.07 (2H, s), 6.86 (2H, d, J=8 Hz), 6.94 (1H, d, J=8 Hz), 7.31 (2H, d, J=8 Hz), 7.4-7.8 (7H, m), 10.3 (1H, br s).

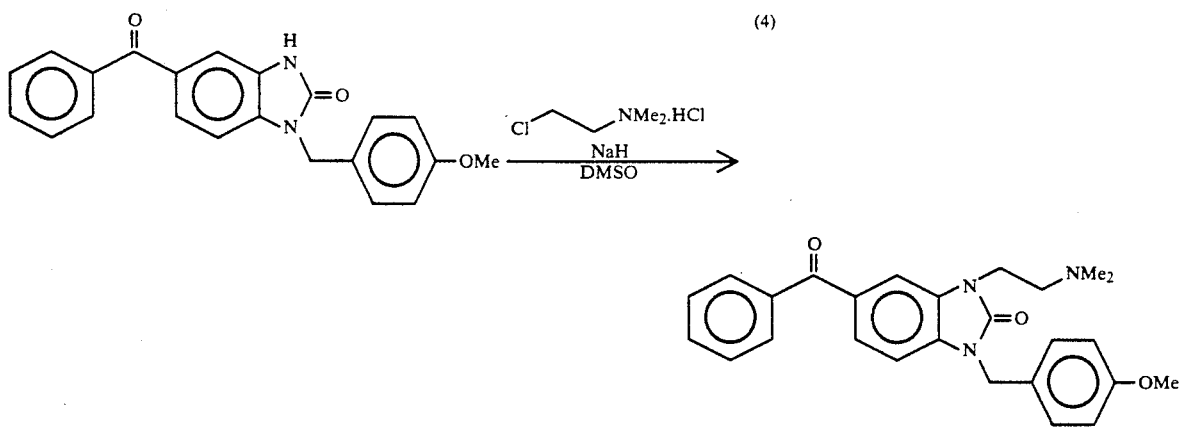

(4)

To a solution of 1.09 g of 5-benzoyl-1-(4-methoxybenzyl)-2H-benzimidazol-2-one in 10 ml of dimethylsulfoxide was added at room temperature 0.27 g of 60% dispersion of sodium hydride in mineral oil. After being stirred for 30 minutes, the reaction mixture was treated with 0.48 g of chloroethyldimethylamine hydrochloride at room temperature for 2 hours and at 55° C for 3 hours, diluted with water and extracted with ethyl acetate. The ethyl acetate layer was extracted with 10% hydrogen chloride. The aqueous layer was alkalized with 20% sodium hydroxide and extracted with ethyl acetate. The ethyl acetate layer was washed with water and brine in turn and dried over anhydrous sodium sulfate. After removal of the solvent in vacuo, the residue was chromatographed on silica gel using chloroform-methanol (15:1) to afford 1.14 g of 5-benzoyl-1,3-dihydro-3-(2-dimethylaminoethyl)-1-(4-methoxybenzyl)-2H-benzimidazol-2-one.

Mass spectrum (m/z): 429 (M+).

NMR (CDCl$_3$) δ: 2.31 (6H, s), 2.68 (2H, t, J=6.8 Hz), 3.77 (2H, s), 4.05 (2H, t, J=6.8 Hz), 5.04 (2H, s), 6.85 (2H, d, J=8.9 Hz), 6.91 (1H, d, J=8.2 Hz), 7.28 (2H, d, J=8.9 Hz), 7.4–7.8 (7H, m).

(6) The following compound was prepared in generally the same manner as Example 1(6).

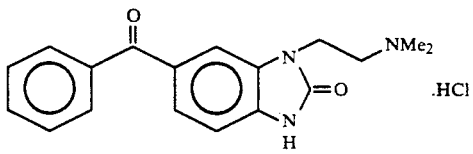

6-Benzoyl-1,3-dihydro-1-(2-dimethylaminoethyl)-2H-benzimidazol-2-one hydrochloride.

Staring compound: 6-Benzoyl-1,3-dihydro-1-(2-dimethylaminoethyl)-2H-benzimidazol-2-one.

mp: 264°–269° C.

| Analysis (for C$_{18}$H$_{20}$N$_3$O$_2$·0.8H$_2$O) | | |
|---|---|---|
| C (%) | H (%) | N (%) |
| Calcd.: 60.01 | 6.04 | 11.66 |
| Found: 59.84 | 5.70 | 12.09 |

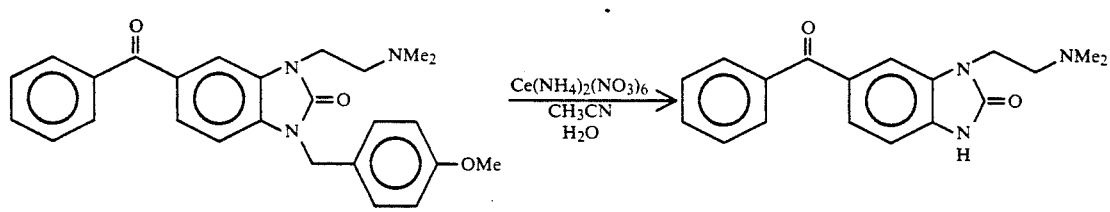

To a solution of 1.11 g of 5-benzoyl-1,3-dihydro-3-(2-dimethylaminoethyl)-1-(4-methoxybenzyl)-2H-benzimidazol-2-one in 20 ml of acetonitrile and 7 ml of water was added 6.43 g of ceric ammonium nitrate. The reaction mixture was stirred at 60° C. for 4 hours, diluted with water and washed with ethyl acetate. After alkalization to pH 9 with 10% sodium hydroxide, the basic material was extracted with chloroform and dried over anhydrous sodium sulfate. Removal of the solvent in vacuo afforded the crude material which was chromatographed on silica gel. Elution with chloroformmethanol (10:1) gave 40 mg of 6-benzoyl-1,3-dihydro-1-(2-dimethylaminoethyl)-2H-benzimidazol-2-one.

Mass spectrum (m/z): 309 (M+).

NMR (CDCl$_3$) δ: 2.36 (6H, s), 2.74 (2H, t, J=7 Hz), 4.05 (2H, t, J=7 Hz), 6.98 (1H, t, J=10 Hz), 7.4–7.6 (5H, m), 7.76 (2H, m), 11.0 (1H, br s).

EXAMPLE 27

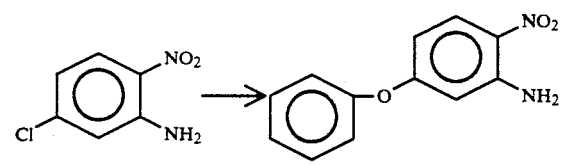

A mixture of 1.09 g of 5-chloro-2-nitroaniline, 10 g of phenol and 2.0 g of anhydrous potassium carbonate was heated at 150° C for 4 days. The reaction mixture was diluted with 1N sodium hydroxide and extracted with ethyl acetate. The ethyl acetate layer was washed with 1N sodium hydroxide, water and brine in turn and dried over anhydrous sodium sulfate. After removal of the solvent, the residue was chromatographed on silica gel using chloroform to give 0.70 g of 2-nitro-5-phenoxyaniline.

Mass spectrum (m/z) 230 (M+).

NMR (CDCl₃) δ: 5.70–6.40 (4H, m), 7.02–7.51 (5H, m), 8.11 (1H, d, J=10 Hz).

(2) The following compound was prepared in generally the same manner as Example 9(2).

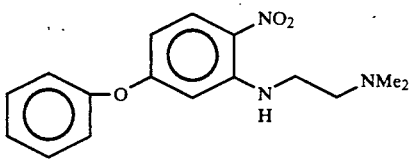

N,N-Dimethyl-N'-(2-nitro-5-phenoxyphenyl)ethylenediamine.

Starting compound: 2-nitro-5-phenoxyaniline.

Mass spectrum (m/z): 302 (M+).

NMR (CDCl₃) δ: 2.26 (6H, s), 2.57 (2H, t, J=6 Hz), 3.10–3.30 (2H, m), 6.15–6.29 (2H, m), 7.03–7.53 (5H, m), 8.02–8.21 (1H, m), 8.43 (1H, br s).

(3) The following compound was prepared in generally the same manner as Example 16(3).

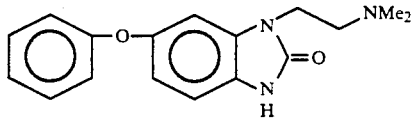

1,3-Dihydro-1-(2-dimethylaminoethyl)-6-phenoxy-2H-benzimidazol-2-one.

Starting compound: N,N-Dimethyl-N,-(2-nitro-5-phenoxyphenyl)ethylenediamine.

Mass spectrum (m/z): 298 (MH+).

NMR (CDCl₃) δ: 2.30 (6H, s), 2.63 (2H, t, J=7 Hz), 3.94 (2H, t, J=7 Hz), 6.70–6.78 (2H, m), 6.92–7.12 (4H, m), 7.24–7.36 (2H, m), 9.46 (1H, s).

(4) The following compound was prepared in generally the same manner as Example 1(6).

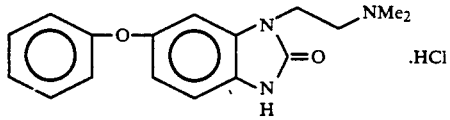

1,3-Dihydro-1-(2-dimethylaminoethyl)-6-phenoxy-2H-benzimidazol-2-one hydrochloride.

Starting compound: 1,3-Dihydro-1-(2-dimethylaminoethyl)-6-phenoxy-2H-benzimidazol-2-one.
mp: 185°–191° C.

| Analysis (for C₁₇H₂₀N₃O₂Cl.0.6H₂O) | | | |
|---|---|---|---|
| C (%) | H (%) | N (%) | Cl (%) |
| Calcd.: 59.25 | 6.20 | 12.19 | 10.29 |
| Found: 59.20 | 6.04 | 12.07 | 10.54 |

EXAMPLE 28

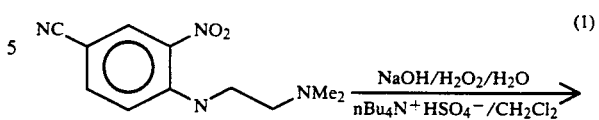

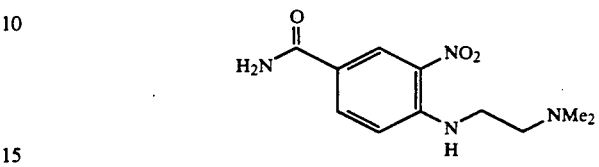

A solution of 0.70 g of N,N-dimethyl-N,-(4-cyano-2-nitrophenyl)ethylenediamine in 5 ml of dichloromethane was treated with 3.0 ml of 20% sodium hydroxide, 3.0 ml of 30% hydrogen peroxide and 0.25 g of tetra-n-butylammonium hydrogen sulfate at room temperature for 1 hour. The dichloromethane layer was separated, washed with water and brine in turn and dried over anhydrous sodium sulfate. Removal of the solvent provided 0.30 g of N,N-dimethyl-N'-(4-carbamoyl-2-nitrophenyl)ethylenediamine.

Mass spectrum (m/z): 253 (MH+).

NMR (CDCl₃) δ: 2.34 (6H, s), 2.66 (2H, t, J=6 Hz), 3.36–3.45 (2H, m), 5.40–5.80 (2H, m), 6.90 (1H, d, J=10 Hz), 8.00 (1H, dd, J=2 and 10 Hz), 8.60 (1H, d, J=2 Hz), 8.70 (1H, br s).

(2) The following compound was prepared in generally the same manner as Example 16(3).

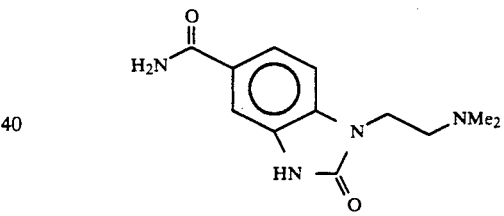

5-Carbamoyl-1,3-dihydro-1-(2-dimethylaminoethyl)-2H-benzimidazol-2-one.

Starting compound: N,N-Dimethyl-N,-(4-carbamoyl-2-nitrophenyl)ethylenediamine

Mass spectrum (m/z) 249 (MH+).

NMR (DMSO-d₆0 δ: 2.20 (6H, s), 2.52 (1H, t, J=7 Hz), 3.88 (2H, t, J=7 Hz), 7.12 (1H, d, J=9 Hz), 7.04–7.20 (1H, m), 7.50–7.70 (2H, m), 7.84 (1H, br s), 11.02 (1H, br s).

(3) The following compound was prepared in generally the same manner as Example 1(6).

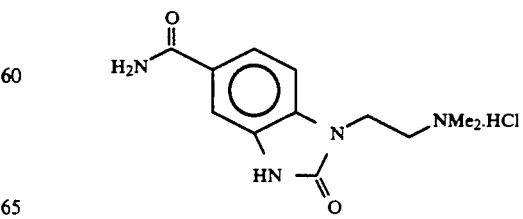

5-Carbamoyl-1,3-dihydro-1-(2-dimethylaminoethyl)-2H-benzimidazol-2-one hydrochloride.

Starting compound: 5-Carbamoyl-1,3-dihydro-1-(2-dimethylaminoethyl)-2H-benzimidazol-2-one.

Mass spectrum (m/z): 249 (MH+-HCl).

NMR (DMSO-$d_6$) δ: 2.60 (6H, s), 2.80–2.92 (2H, m), 4.12–4.36 (2H, m), 7.16–7.40 (2H, m), 7.52–7.76 (2H, m), 7.92 (1H, br s), 10.40 (1H, br s), 11.26 (1H, s).

DOSAGE FORM EXAMPLE 1
[Inhalant]
Powder inhalant

| | |
|---|---|
| Compound of Example 12(5) | 1 mg |
| Lactose | 39 mg |
| | 40 mg |

The compound of Example 12(5) (1 g) is uniformly blended with 39 g of lactose and the mixture is comminuted, sieved and filled into No. 3 capsules using a capsule filling machine to give powder inhalant dosage units.

DOSAGE FORM EXAMPLE 2
[Inhalant]
Suspension

| | |
|---|---|
| Compound of Example 12(5) | 0.15 g |
| Sorbitan trioleate | 0.21 g |
| Dichloromonofluoromethane | 5.16 g |
| Dichlorotetrafluoroethane | 5.16 g |
| Dichlorodifluoromethane | 10.32 g |
| | 21.0 g |

The compound of Example 12(5) (150 g) is uniformly blended with 210 g of sorbitan trioleate. The resulting mixture is distributed in 0.36 g portions into 20 ml aluminum cans. A valve device is inserted into each can. The cans are then sealed and the specified amounts of propellants are forced into each container under pressure using a pressure gas buret to give aerosols.

DOSAGE FORM EXAMPLE 3
[Inhalant]
Solution

| | |
|---|---|
| Compound of Example 12(5) | 0.15 g |
| Distilled water | 4.2 ml |
| Benzalkonium chloride | 0.01 g |
| Dichloromonofluoromethane | 5.16 g |
| Dichlorotetrafluoroethane | 5.16 g |
| Dichlorodifluoromethane | 10.32 g |
| | 25.0 g |

The compound of Example 12(5) (150 g) is uniformly blended with 10 g of benzalkonium chloride and 4.2 liters of distilled water. The resulting mixture is distributed in 4.36 g portions into 20 ml aluminum cans. Following insertion of a valve device into each can, the cans are sealed and then the prescribed amounts of propellants are filled into the containers under pressure using a pressure gas buret to give aerosols.

DOSAGE FORM EXAMPLE 4
Tablet

| | |
|---|---|
| Compound of Example 12(5) | 100 mg |
| Lactose | 56 mg |
| Corn starch | 37 mg |
| Hydroxypropylcellulose | 6 mg |
| Magnesium stearate | 1 mg |
| Total | 200 mg |

The compound of Example 12(5) (100 g) is uniformly blended with 56 g of lactose and 37 g of corn starch, followed by addition of 60 g of a 10% hydroxypropylcellulose solution. The resulting mixture is granulated by the wet method. The granules are sieved and dried. Then, 1 g of magnesium stearate is added to and mixed with the dried granules and the mixture is tableted using a die and punch of 8 mm and 6.4R to give tablets.

DOSAGE FORM EXAMPLE 5
Capsule

| | |
|---|---|
| Compound of Example 12(5) | 50 mg |
| Crystalline cellulose | 40 mg |
| Crystalline lactose | 109 mg |
| Magnesium stearate | 1 mg |
| Total | 200 mg |

The compound of Example 12(5) (50 g), 40 g of crystalline cellulose, 109 g of crystalline lactose and 1 g of magnesium stearate are uniformly mixed up together and the mixture is filled in 200 mg portions into No. 3 capsules using a capsule filling machine.

DOSAGE FORM EXAMPLE 6
Lyophilized preparation
per vial

| | |
|---|---|
| Compound of Example 12(5) | 25 mg |
| D-Mannitol | 33 mg |
| Total | 58 mg |

To 800 ml of water was added 25 g of the compound of Example 12(5) and 33 g of D-mannitol and dissolved in that order, diluted with water to make 1, and the solution is aseptically filtered, distributed in 1 ml portions into vials and lyophilized to give injectable dosage units to be dissolved before use.

While the invention has been described in detail and with reference to specific embodiments thereof, it will be apparent to one skilled in the art that the various changes and modifications can be made therein without departing from the spirit and scope thereof.

What is claimed is:

1. A method of promoting pulmonary surfactant secretion in a patient which comprises administering to said patient a therapeutically effective amount of a pharmaceutical composition comprised of a pharmacologically effective amount of the benzimidazolinone derivative of formula (I)

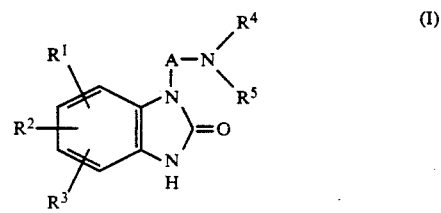

wherein $R^1$, $R^2$ and $R^3$, which may be the same or different, each is a hydrogen atom, a halogen atom, a lower alkyl group, a halo-lower alkyl group, a hydroxy-lower alkyl group, a hydroxyl group, a lower alkoxy group, an aryloxy group, a cyano group, a carboxyl group, a lower alkoxycarbonyl group, a carbamoyl group, a nitro group or a nitrogen-containing 5- or 6-membered heterocyclic group; A is an ethylene group which may optionally have at least one branch; $R^4$ and $R^5$, which may be the same or different, each is a lower alkyl group or $R^4$ and $R^5$ may be combined together with the adjacent nitrogen atom to form a pyrrolidinyl group, a piperidino group or a morpholino group provided that when

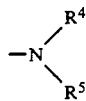

is a piperidino group or a diethylamino group, at least one of $R^1$, $R^2$ and $R^3$ is other than a hydrogen atom, or a pharmaceutically acceptable salt thereof and a pharmaceutically acceptable carrier therefor.

2. The method of claim 1 wherein $R^4$ and $R^5$ are combined together with the adjacent nitrogen atom to form a pyrrolidinyl group.

3. The method of claim 1 wherein $R^4$ and $R^5$ are combined together with the adjacent nitrogen atom to form a piperidino group.

4. The method of claim 1 wherein $R^4$ and $R^5$ are combined together with the adjacent nitrogen atom to form a morpholino group.

5. The method of claim 1 wherein $R^1$ is halogen, $R^2$ and $R^3$ are hydrogen, A is an ethylene group, and $R^4$ and $R^5$ are combined together with the adjacent nitrogen atom to form a pyrrolidinyl group.

6. The method of claim 2 wherein the benzimidazolinone derivative of formula (I) is 6-chloro-1,3-dihydro-1-[2-(1-pyrrolidinyl)ethyl]-2H-benzimidazol-2-one hydrochloride.

7. The method of claim 3 wherein the benzimidazolinone derivative of formula (I) is 6-chloro-1,3-dihydro-1-(2-piperidinoethyl)-2H-benzimidazol-2-one.

8. The method of claim 4 wherein the benzimidazolinone derivative of formula (I) is 6-chloro-1,3-dihydro-1-(2-morpholinoethyl)-2H-benzimidazol-2-one hydrochloride.

* * * * *